(12) United States Patent
Salvati et al.

(10) Patent No.: US 10,799,105 B2
(45) Date of Patent: Oct. 13, 2020

(54) DIGITAL COLPOSCOPE SYSTEM

(71) Applicant: Welch Allyn, Inc., Skaneateles Falls, NY (US)

(72) Inventors: Jon R. Salvati, Skaneateles, NY (US); Raymond A. Lia, Auburn, NY (US); Ervin Goldfain, Syracuse, NY (US); Robert L. Vivenzio, Auburn, NY (US); Kenzi L. Mudge, Syracuse, NY (US); David J. Maier, Skaneateles, NY (US)

(73) Assignee: WELCH ALLYN, INC., Skaneateles Falls, NY (US)

( * ) Notice: Subject to any disclaimer, the term of this patent is extended or adjusted under 35 U.S.C. 154(b) by 0 days.

(21) Appl. No.: 16/014,870

(22) Filed: Jun. 21, 2018

(65) Prior Publication Data

US 2018/0296082 A1    Oct. 18, 2018

Related U.S. Application Data

(63) Continuation of application No. 14/557,146, filed on Dec. 1, 2014, now Pat. No. 10,028,649.

(60) Provisional application No. 61/910,545, filed on Dec. 2, 2013.

(51) Int. Cl.
| | |
|---|---|
| *A61B 1/303* | (2006.01) |
| *A61B 1/00* | (2006.01) |
| *A61B 1/32* | (2006.01) |

(52) U.S. Cl.
CPC ........... *A61B 1/303* (2013.01); *A61B 1/0005* (2013.01); *A61B 1/00009* (2013.01); *A61B 1/00039* (2013.01); *A61B 1/00052* (2013.01); *A61B 1/00108* (2013.01); *A61B 1/00149* (2013.01); *A61B 1/32* (2013.01)

(58) Field of Classification Search
CPC combination set(s) only.
See application file for complete search history.

(56) References Cited

U.S. PATENT DOCUMENTS

| | | |
|---|---|---|
| 5,026,368 A | 6/1991 | Adair |
| 6,097,848 A | 8/2000 | Salvati |
| 6,106,457 A * | 8/2000 | Perkins .............. A61B 1/00041 396/312 |

(Continued)

OTHER PUBLICATIONS

Examiner, http://www.welchallyn.com/promotions/iExaminer/index.html, © 2014 WelchAllyn® (4 pages).

(Continued)

*Primary Examiner* — Tsung Yin Tsai
(74) *Attorney, Agent, or Firm* — Merchant & Gould P.C.

(57) ABSTRACT

An example system to capture digital images includes: a colposcope device configured to capture a digital image during a colposcopy procedure; and an image processing module programmed to digitally process the digital image, including: a filter module programmed to filter certain aspects of the digital image; and an overlay module programmed to allow the digital image to be annotated. In other examples, colposcope devices include: a cradle, the cradle being configured to hold a portable computing device, the cradle including an aperture; and an optical capture device, the optical capture device including a constant magnification lens system, the constant magnification lens system being configured to direct light through the aperture.

16 Claims, 23 Drawing Sheets

(56) References Cited

U.S. PATENT DOCUMENTS

| | | | |
|---|---|---|---|
| 6,147,705 A | 11/2000 | Krauter et al. | |
| 6,277,067 B1* | 8/2001 | Blair | A61B 1/00041 348/77 |
| 6,359,644 B1* | 3/2002 | Salvati | A61B 5/1076 348/65 |
| 6,393,431 B1* | 5/2002 | Salvati | A61B 1/00041 |
| 6,589,168 B2 | 7/2003 | Thompson | |
| 6,595,917 B2 | 7/2003 | Nieto | |
| 6,712,761 B2 | 3/2004 | Borodulin et al. | |
| 6,896,653 B1 | 5/2005 | Vail, III et al. | |
| 7,515,952 B2 | 4/2009 | Balas et al. | |
| 8,045,770 B2 | 10/2011 | Reeves et al. | |
| 8,096,945 B2 | 1/2012 | Buchok et al. | |
| 8,554,307 B2 | 10/2013 | Razzaque et al. | |
| 8,638,995 B2 | 1/2014 | Greenstein et al. | |
| 2004/0152752 A1 | 8/2004 | Chong et al. | |
| 2004/0186357 A1* | 9/2004 | Soderberg | A61B 5/0013 600/300 |
| 2004/0208385 A1 | 10/2004 | Jiang | |
| 2004/0208390 A1 | 10/2004 | Jiang et al. | |
| 2004/0252870 A1 | 12/2004 | Reeves et al. | |
| 2005/0031643 A1 | 2/2005 | Szalay et al. | |
| 2005/0234305 A1 | 10/2005 | Licciardi | |
| 2005/0234526 A1 | 10/2005 | Gilhuly et al. | |
| 2007/0161876 A1* | 7/2007 | Bambot | G01J 3/027 600/310 |
| 2008/0303899 A1* | 12/2008 | Berci | H04N 5/2254 348/74 |
| 2009/0076368 A1* | 3/2009 | Balas | A61B 1/00149 600/407 |
| 2009/0082695 A1* | 3/2009 | Whitehead | A61B 1/303 600/562 |
| 2009/0220122 A1 | 9/2009 | Richards et al. | |
| 2010/0004539 A1 | 1/2010 | Chen et al. | |
| 2010/0305406 A1* | 12/2010 | Braun | H01C 17/12 600/202 |
| 2011/0243402 A1 | 10/2011 | Kadir | |
| 2011/0311109 A1 | 12/2011 | Demarais et al. | |
| 2012/0059220 A1* | 3/2012 | Holsing | A61B 34/20 600/109 |
| 2012/0123205 A1 | 5/2012 | Nie et al. | |
| 2012/0232352 A1 | 9/2012 | Lin et al. | |
| 2013/0018276 A1 | 1/2013 | Zaldivar et al. | |
| 2013/0083984 A1 | 4/2013 | Chabanas et al. | |
| 2013/0128223 A1 | 5/2013 | Wood et al. | |
| 2013/0208955 A1 | 8/2013 | Zhao et al. | |
| 2013/0300919 A1* | 11/2013 | Fletcher | H04M 1/21 348/360 |
| 2014/0005477 A1 | 1/2014 | Gupta et al. | |
| 2014/0029815 A1 | 1/2014 | Kadir et al. | |
| 2014/0031702 A1 | 1/2014 | Diaz Sanchez et al. | |
| 2014/0051923 A1* | 2/2014 | Mirza | A61B 1/00195 600/103 |
| 2014/0111634 A1* | 4/2014 | Mueckl | H04N 5/2252 348/82 |
| 2014/0142433 A1* | 5/2014 | Greenstein | A61B 1/042 600/473 |
| 2015/0103317 A1* | 4/2015 | Goldfain | A61B 3/10 351/207 |
| 2015/0150440 A1* | 6/2015 | Salvati | A61B 1/303 600/109 |
| 2016/0051142 A1* | 2/2016 | Howes | A61B 3/14 351/245 |
| 2017/0020627 A1* | 1/2017 | Tesar | G02B 27/00 |
| 2017/0303857 A1* | 10/2017 | Perkins | F16B 1/00 |
| 2017/0336619 A1* | 11/2017 | Cheng | G02B 21/368 |
| 2018/0092530 A1* | 4/2018 | Hart | A61B 3/0025 |

OTHER PUBLICATIONS

Examiner™ Quick Reference, http://www.welchallyn.com/content/dam/welchallyn/documents/upload-docs/Product-Literature/Promotion-Flyer/iExaminer/iExaminer_Instruction_Manual.pdf, © 2013 WelchAllyn, Inc. (2 pages).

Medical Zone, "Mini colposcope Belson BS2BELBS2," http://zonemedical.com.au/medical-equipment/Womens-Health/Belson-Mini-Colposcope-BS2-BELBS2.html, Mar. 2, 2014 (3 pages).

VedaScope, "VedaScope MKII," http://pacificei.com/, Mar. 1, 2014 (1 page).

Hill, et al., "Sheathed versus standard speculum for visualization of the cervix," International Journal of Gynecology & Obstretics; Feb. 2014 online, http://www.ncbi.nlm.nik.gov/pubmed/24565103 (2 pages).

Quinn, M. J., "An illuminated vaginal speculum," American Journal Obstetrics Gynecology; Jan. 1999;180 (1 Pt 1):33-4 (2 pages).

KleenSpec® Speculum Lighting Systems, https://www.welchallyn.com/apps/products/product.jsp?id=11-ac-100-0000000001199, Mar. 1, 2014 (1 page).

\* cited by examiner

ABSTRACT
DIGITAL COLPOSCOPE SYSTEM

BACKGROUND

A colposcope device is a medical diagnostic tool used to image the cervix and tissues of the vagina and vulva. This imaging is used to detect abnormalities, such as malignant lesions. The colposcope device typical includes a camera that is used to capture the images and a display used to display the images obtained by the colposcope device.

SUMMARY

In one aspect, a system to capture digital images includes: a colposcope device configured to capture a digital image during a colposcopy procedure; and an image processing module programmed to digitally process the digital image, including: a filter module programmed to filter certain aspects of the digital image; and an overlay module programmed to allow the digital image to be annotated.

In another aspect, a method for processing a digital image captured by a colposcope device includes: receiving the digital image from the colposcope device; filtering, by a computing device, the digital image; and allowing a user to annotate the digital image.

In yet another aspect, a method for processing a digital image captured by a colposcope device includes: receiving the digital image from the colposcope device; filtering, by a computing device, the digital image, including providing a green filter; and allowing a user to annotate the digital image, including: providing a digital caliper; allowing the user to manipulate the digital caliper; and providing a length of a portion of the digital image identified by the digital caliper.

In yet another aspect, a housing for a colposcope device includes: a cradle, the cradle being configured to hold a portable computing device, the cradle including an aperture; and an optical capture device, the optical capture device including a constant magnification lens system, the constant magnification lens system being configured to direct light through the aperture.

In yet another aspect a colposcope device includes: a portable computing device, the portable computing device including a camera, a display screen, and a processor; and a housing, the housing including a cradle and an optical capture device, the cradle being configured to hold the portable computing device, the cradle including an aperture, the aperture being configured to permit light to reach the camera, the optical capture device including a constant magnification lens system, the constant magnification lens system being configured to direct light through the aperture.

In yet another aspect, a colposcope system includes: a speculum, the speculum including a port and an illumination device; a portable computing device, the portable computing device including a camera, a display screen, and a processor; and a housing, the housing including: a cradle, the cradle being configured to hold the portable computing device, the cradle including an aperture, the aperture being configured to permit light to reach the camera; an optical capture device, the optical capture device including a constant magnification lens system, the constant magnification lens system being configured to direct light through the aperture; wherein the optical capture device is configured to capture light through the port of the speculum.

In yet another aspect, a colposcope device includes: a portable computing device, the portable computing device including a camera, a display screen, and a processor, the portable computing device being configured to capture a digital image during a colposcopy procedure; a housing, the housing including a cradle and an optical capture device, the cradle being configured to hold the portable computing device, the cradle including an aperture, the aperture being configured to permit light to reach the camera, the optical capture device including a constant magnification lens system, the constant magnification lens system being configured to direct light through the aperture; and an image processing module programmed to digitally process the digital image, including: a filter module programmed to filter certain aspects of the digital image; and an overlay module programmed to allow the digital image to be annotated.

DETAILED DESCRIPTION

The present disclosure relates to colposcope systems and methods for processing digital images from colposcope devices.

Figure 1:
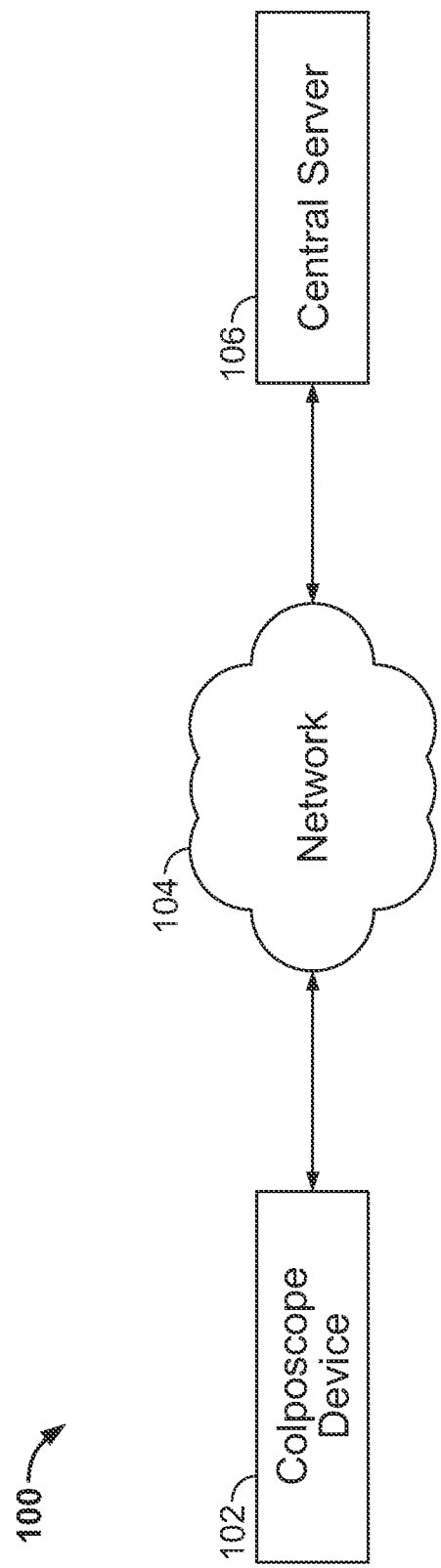
FIG. 1 shows an example system for performing colposcopy procedures.

FIG. 1 is an example system 100 for performing colposcopy procedures. In this example, a colposcope device 102 is used to capture, process, and display the digital images.

In addition, in some embodiments, the colposcope device 102 is configured to send data associated with the digital images to a central server 106. For example, the colposcope device 102 can be programmed to send digital images to the central server 106 for additional processing and/or storage in an electronic medical record (EMR).

The colposcope device 102 and the central server 106 communicate through a network 104. In one example, the colposcope device 102 and network 104 are part of a CONNEX™ system from Welch Allyn of Skaneateles Falls, N.Y., although other systems can be used. In such an example, the monitor devices communicate through known protocols, such as the Welch Allyn Communications Protocol (WACP). WACP uses a taxonomy as a mechanism to define information and messaging. Taxonomy can be defined as description, identification, and classification of a semantic model. Taxonomy as applied to a classification scheme may be extensible. Semantic class-based modeling utilizing taxonomy can minimize the complexity of data description management by limiting, categorizing, and logically grouping information management and operational functions into families that contain both static and dynamic elements.

In another example, the central server 106 can be a distributed network, commonly referred to as a "cloud" server. The colposcope device 102 communicates with the cloud server through non-proprietary, industry standard messaging. Data encryption is also based on industry standards.

The network 104 is an electronic communication network that facilitates communication between the colposcope device 102 and the central server 106. An electronic communication network is a set of computing devices and links between the computing devices. The computing devices in the network use the links to enable communication among the computing devices in the network. The network 104 can include routers, switches, mobile access points, bridges, hubs, intrusion detection devices, storage devices, stand-alone server devices, blade server devices, sensors, desktop computers, firewall devices, laptop computers, handheld computers, mobile telephones, and other types of computing devices.

In various embodiments, the network 104 includes various types of links. For example, the network 104 can include wired and/or wireless links. Furthermore, in various embodiments, the network 104 is implemented at various scales. For example, the network 104 can be implemented as one or more local area networks (LANs), metropolitan area networks, subnets, wide area networks (such as the Internet), or can be implemented at another scale.

The colposcope device 102 and the central server 106 are computing devices. A computing device is a physical, tangible device that processes data. Example types of computing devices include personal computers, standalone server computers, blade server computers, mainframe computers, handheld computers, smart phones, special purpose computing devices, and other types of devices that process data.

Computing devices can include at least one central processing unit ("CPU"), a system memory, and a system bus that couples the system memory to the CPU. The system memory includes a random access memory ("RAM") and a read-only memory ("ROM"). A basic input/output system containing the basic routines that help to transfer information between elements within the device, such as during startup, is stored in the ROM. The device further includes a mass storage device. The mass storage device is able to store software instructions and data.

The mass storage device and its associated computer-readable data storage media provide non-volatile, non-transitory storage for the device. Although the description of computer-readable data storage media contained herein refers to a mass storage device, such as a hard disk or CD-ROM drive, it should be appreciated by those skilled in the art that computer-readable data storage media can be any available non-transitory, physical device or article of manufacture from which the device can read data and/or instructions.

Computer-readable data storage media include volatile and non-volatile, removable and non-removable media implemented in any method or technology for storage of information such as computer-readable software instructions, data structures, program modules or other data. Example types of computer-readable data storage media include, but are not limited to, RAM, ROM, EPROM, EEPROM, flash memory or other solid state memory technology, CD-ROMs, digital versatile discs ("DVDs"), other optical storage media, magnetic cassettes, magnetic tape, magnetic disk storage or other magnetic storage devices, or any other medium which can be used to store the desired information and which can be accessed by the device.

The computing device can also include an input/output controller for receiving and processing input from a number of other devices, including a keyboard, a mouse, a touch user interface display screen, or another type of input device. Similarly, the input/output controller provides output to a touch user interface display screen, a printer, or other type of output device.

Figure 2:
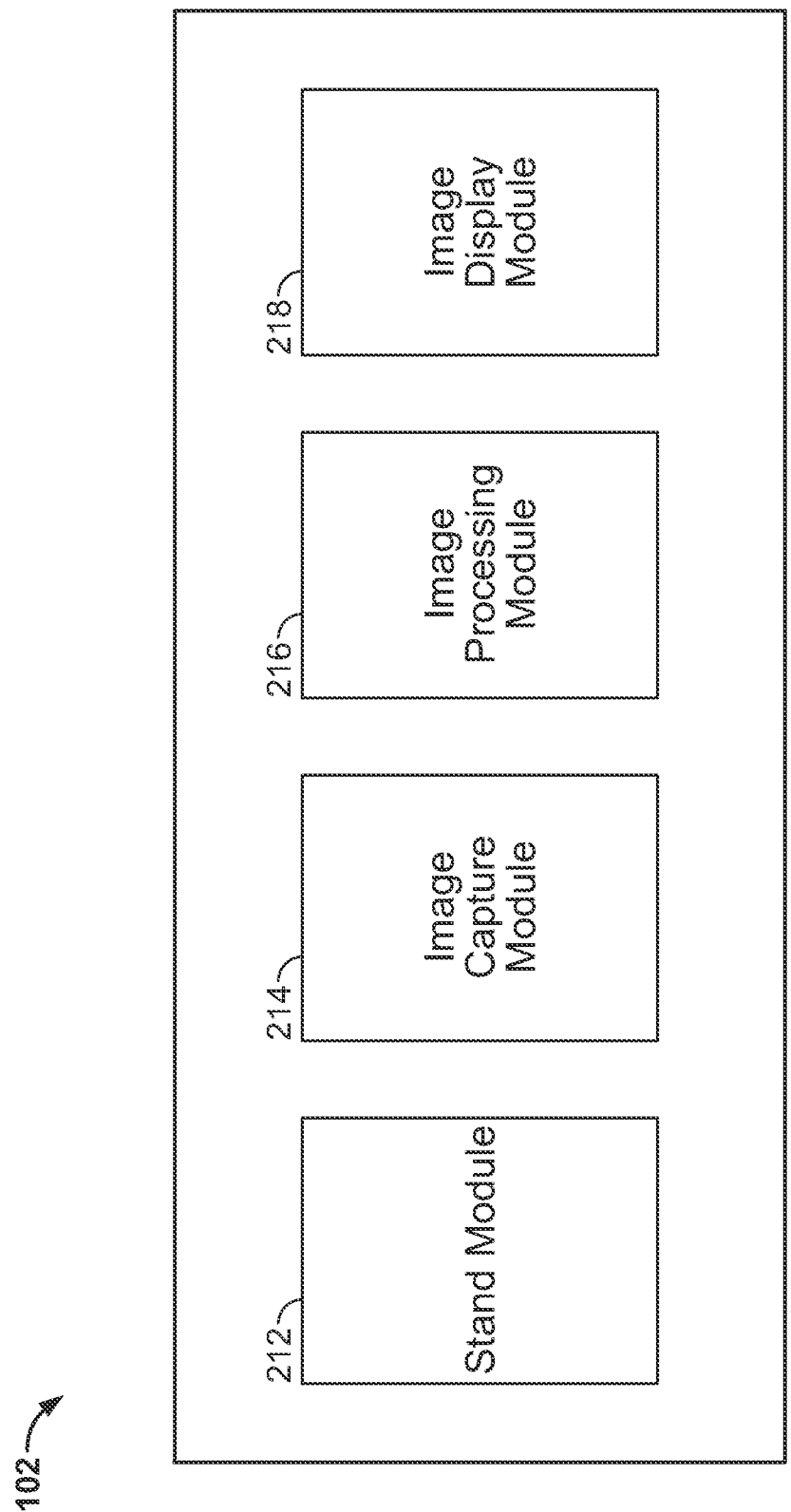
FIG. 2 shows an example colposcope device of the system of FIG. 1.

Referring now to FIG. 2, the colposcope device 102 is shown in more detail. In this example, the colposcope device 102 includes a stand module 212, an image capture module 214, an image processing module 216, and an image display module 218.

The stand module 212 is a physical structure that holds other components of the colposcope device 102 during imaging. In some embodiments, the stand can be manipulated to provide a proper height and orientation when imaging occurs. The stand module is shown and described in greater detail with reference to FIGS. 8-9 and 15-22.

The image capture module 214 can include one or more lenses and a computing device including a digital camera to capture the images. In one example, the computing device is a handheld or tablet computing device, such as an iPhone or iPad from Apple Inc. of Cupertino, Calif. Other computing devices can be used.

In the examples shown, the image that is captured is a digital image. This image can be captured in a variety of formats, such as JPEG, BITMAP, TIFF, etc.

In examples described herein, the image processing module 216 of the colposcope device 102 manipulates the digital images captured by the image capture module 214. The image display module 218 displays one or more of the digital images in original and/or manipulated formats.

For example, the digital images can be displayed on a display of the computing device, such as the screen of the iPhone or iPad devices. For example, in one implementation, the image capture module 214, the image processing module 216, and the image display module 218 are implemented as a software application running on an iPad device. The camera of the iPad device is used by the image capture module 214 to capture the digital image. Other configurations are possible.

Figure 3:
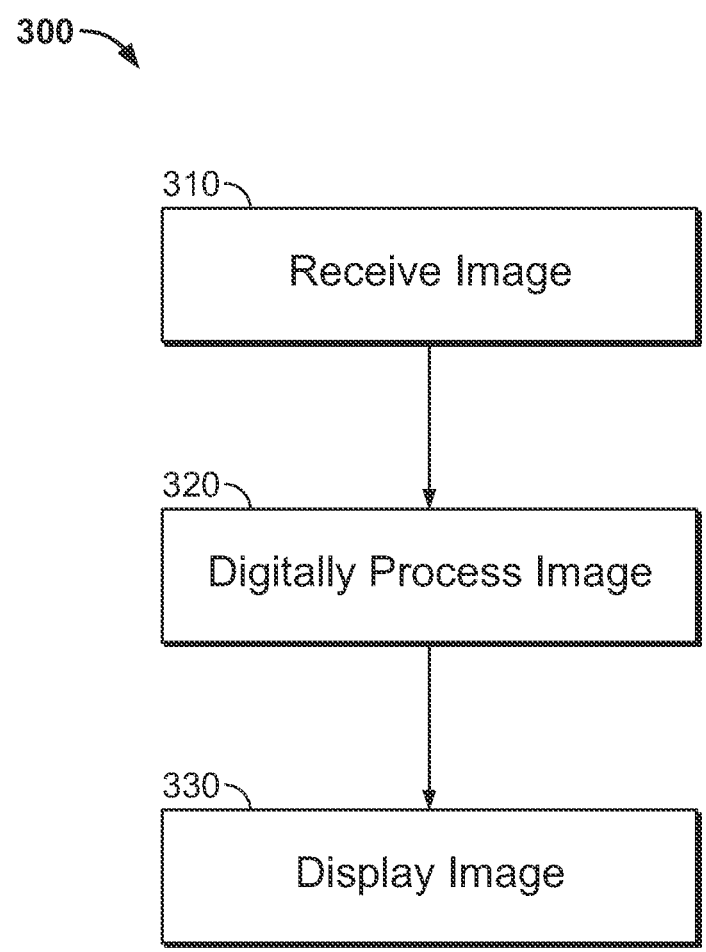
FIG. 3 shows an example method for processing digital images taken by the colposcope device of FIG. 2.

Referring now to FIG. 3, an example method for processing digital images taken by the colposcope device 102 is shown.

At operation 310, a digital image is received, such as from the image capture module 214.

Next, at operation 320, the digital image is processed by, for example, the image processing module 216. In these examples, the image is in a digital format (e.g., JPEG, BITMAP, TIFF, etc.), so the digital image can be processed using various techniques. These techniques are described further below in reference to FIGS. 4-5.

Finally, at operation 330, the manipulated digital image is displayed by, for example, the image display module 218.

Figure 4:
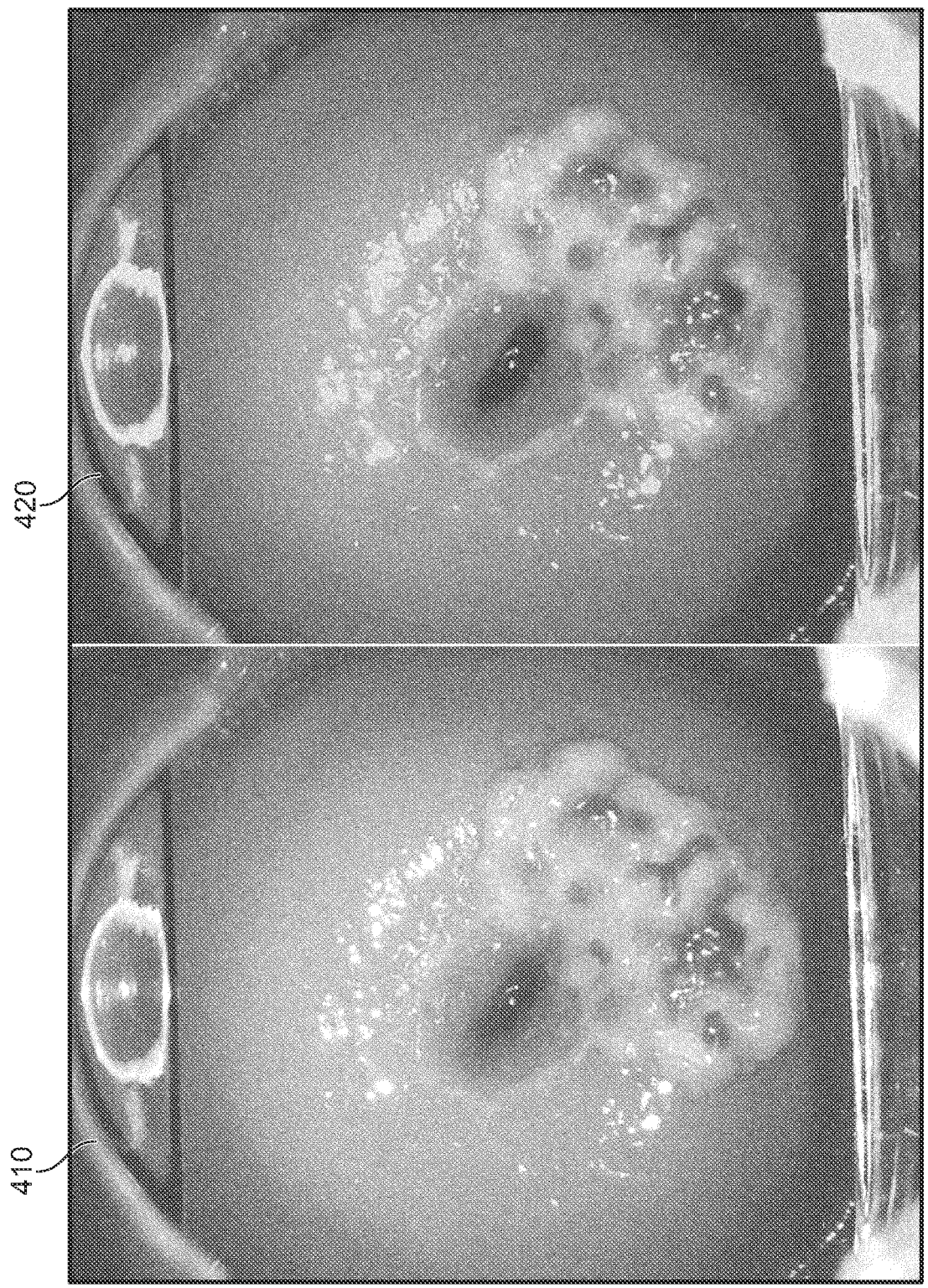
FIG. 4 shows an example digital image before and after manipulation by the colposcope device of FIG. 2.

Referring now to FIG. 4, an example of the digital image processing performed by the image processing module 216 is shown. In this example, the digital image is filtered to better highlight specific aspects of the image, such as any lesions shown thereon.

Specifically, the digital image uses the red, green, blue (RGB) color model and is comprised of three "channels" of intensity values: red, green, and blue. Since digital images captured with the colposcope device are of this form, a green filter is used remove the red channel from the image. Thus, a full color digital image 410 is transformed into a digital image 420 with only hues of green and blue, thus allowing high-contrast visualization of blood vessels in black. This way hemorrhages and micro-aneurysms stand out and can be easily identified. Other example filters, such as an infrared filter or a cobalt (blue) filter can also be applied.

One example of a filtering technique that is applied to analog images (i.e., video captured by an analog video camera) is described in U.S. Pat. No. 6,147,705 filed on Aug. 20, 1996 and entitled "Apparatus and method for video colposcope with electronic green filter," the entirety of which is hereby incorporated by reference.

The digital image 420 can provide a better contrast so that aspects of the digital image are highlighted. In this example, the lesion in the digital image 420 is better contrasted in the digital image 420 as compared to the image 410.

Other filtering techniques are possible. Examples of such techniques that are applied to analog images (i.e., video captured by an analog video camera) are described in U.S. Pat. No. 6,097,848 filed on Nov. 3, 1997 and entitled "Noise reduction apparatus for electronic edge enhancement," the entirety of which is hereby incorporated by reference.

Figure 5:
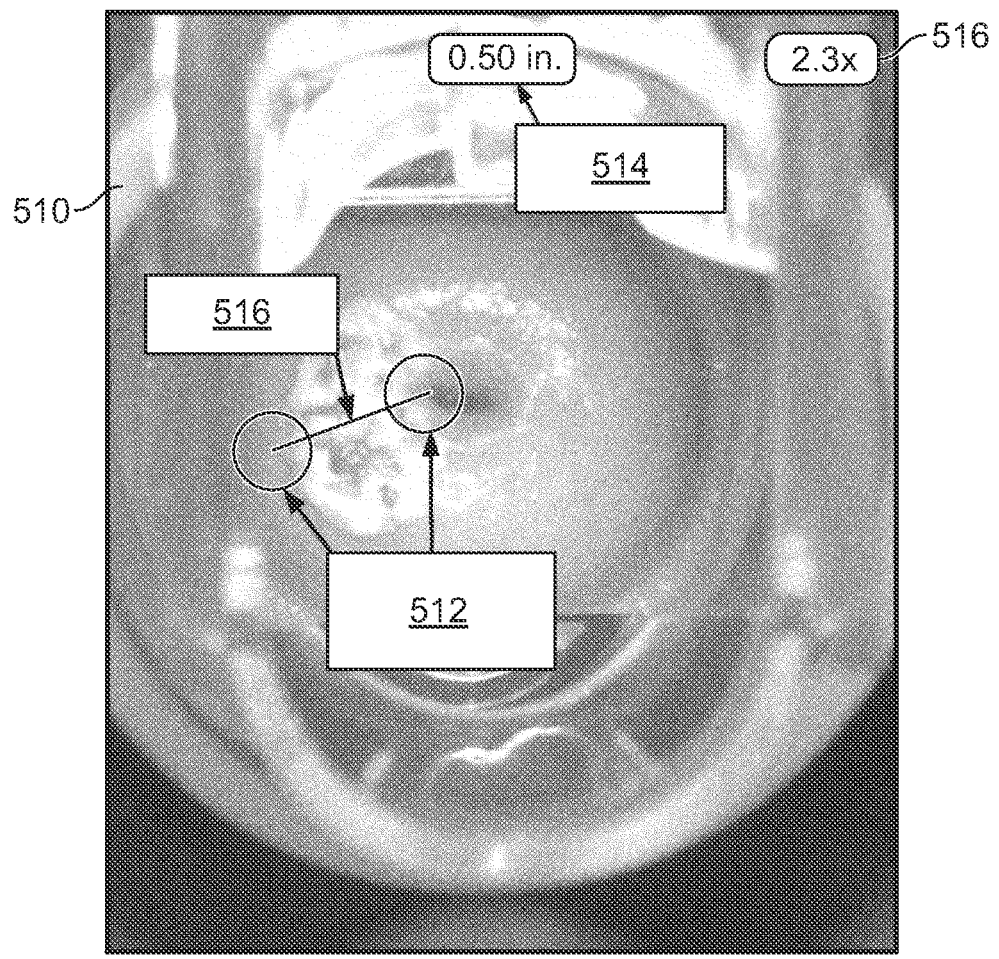
FIG. 5 shows an example digital image after manipulation using the colposcope device of FIG. 2.

Referring now to FIG. 5, an example digital image 510 is shown after manipulation by the user of the colposcope device 102. Specifically, the colposcope device 102 provides digital calipers 512 that allow the user to measure certain aspects of the digital image.

A formula is derived to calculate the real-world size of each pixel in the digital image 510. One example of a determination that is applied to analog images (i.e., video captured by an analog video camera) is described in U.S. Pat. No. 6,359,644 filed on Sep. 1, 1998 and entitled "Measurement system for video colposcope," the entirety of which is hereby incorporated by reference.

Each point of the digital calipers 512 is positioned on the screen, and the length 516 between them is measured in pixels. The user can manipulate the points of the digital calipers 512 using one or two fingers to position the points on the screen at the desired positions.

Using the formula, the found pixel length is converted into a human understandable measurement, such as inches or centimeters, and displayed on the screen as a length 514 (e.g., 0.50 inches).

The colposcope device 102 maintains this measurement regardless of digital zoom level. For example, the zoom level of the image 510 is currently at 2.3× the original image zoom. If the zoom is increased or decreased, the digital calipers 512 are modified to maintain the same measurement length.

In other examples, other information can be added to the digital image. In one alternative embodiment, annotations can be added to the digital image. The annotations can be free form and/or preset input.

This includes information such as highlighting of certain regions of the digital image, capturing notes about the digital image, etc. The annotations can be created using a keyboard and/or using a stylus/pen or finger to annotate the digital image.

In another alternative, an algorithm is used to automatically determine the edges of an object depicted in a digital image, such as a lesion. In such an example, the size and area of the object can be calculated.

Figure 6:
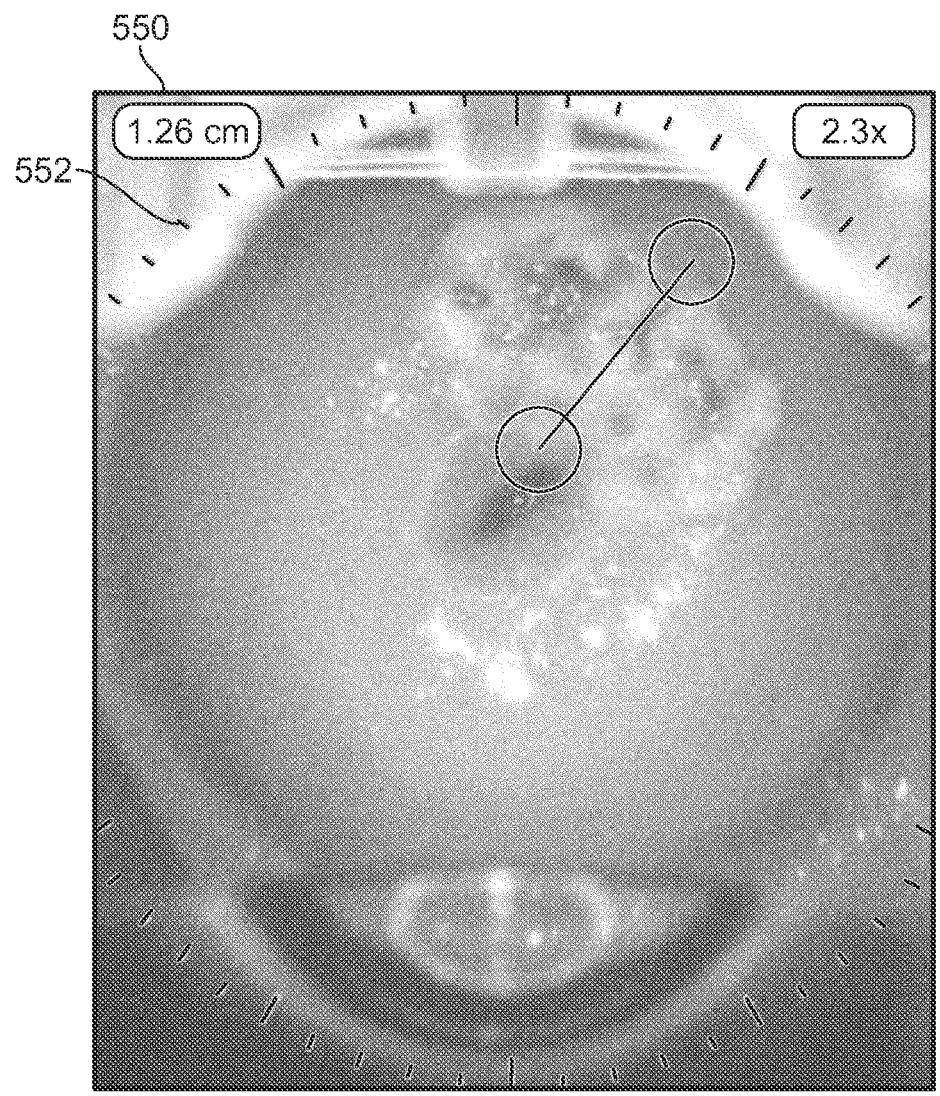
FIG. 6 shows an example digital image including an example clock face overlay.

Referring now to FIG. 6, another example an example digital image 550 is shown from the colposcope device 102. The digital image 550 includes an overlay this is applied to the digital image. In this example, the overlay is a clock face overlay 552 which defines different quadrants of the digital image. In this manner, the user can reference the relevant portion of the clock face overlay 552 (e.g., portion of lesion located at 1 o'clock, etc.) when noting features of the digital image for later consideration, such as in patient notes.

The manipulated digital images can be stored separately from the raw or original digital images. The digital images can be stored locally on the colposcope device and/or stored on the central server 106, such as in the patient's EMR.

Figure 7:
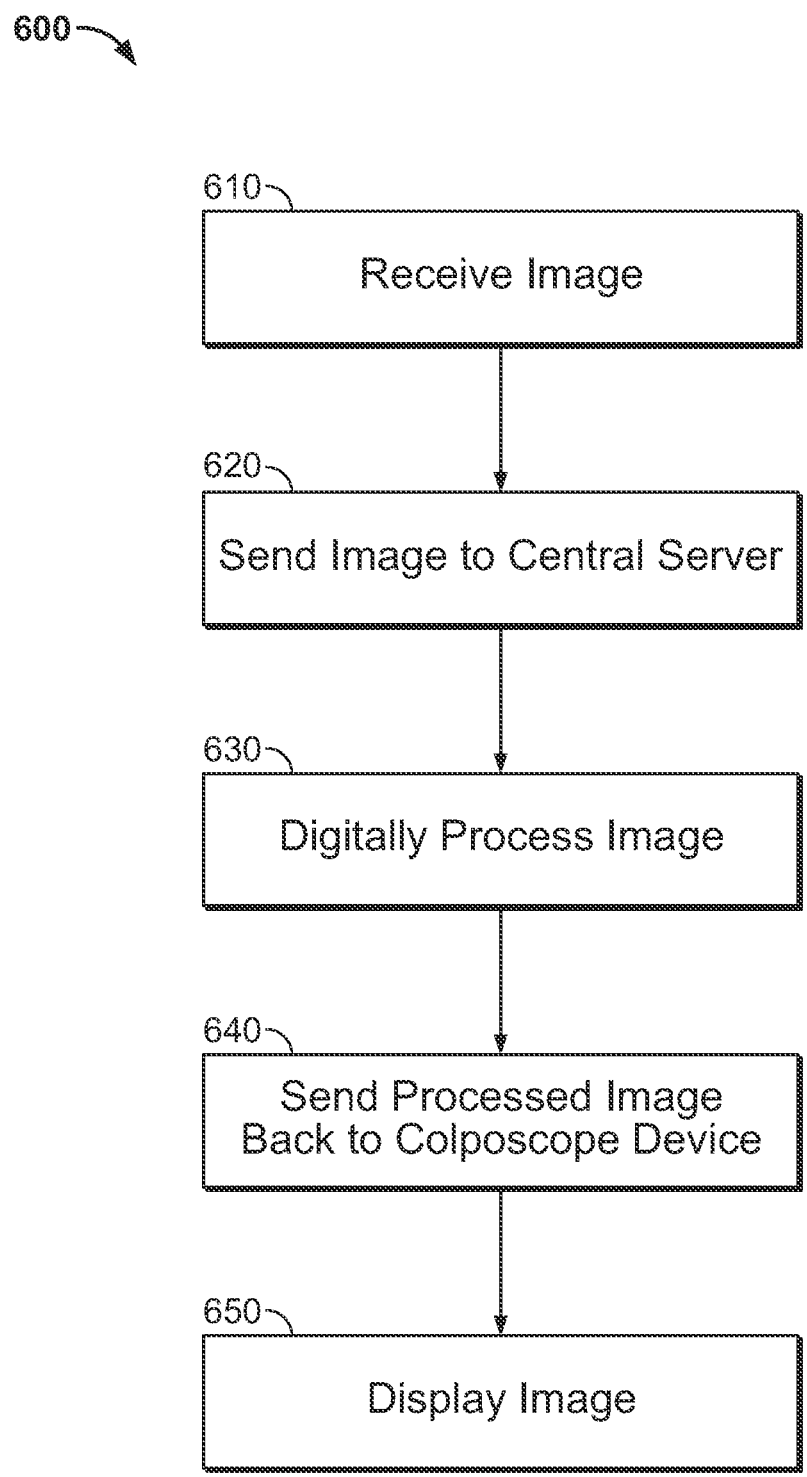
FIG. 7 shows an example method for processing digital images taken by the colposcope device of FIG. 2.

Referring now to FIG. 7, an example method for processing digital images taken by the colposcope device 102 is shown.

At operation 610, a digital image is received, such as from the image capture module 214.

Next, at operation 620, the digital image is sent to a central server, such as central server 106, for further processing.

At operation 630, the central server processes the digital image. It can be advantageous to have the digital image processed at the central server 106 as opposed to on the colposcope device 102 because the central server 106 can include additional resources (e.g., processing power and memory) that allow complex and process-intensive routines to be run when processing the image.

For example, various machine vision techniques can be used to identify aspects of the digital image for further consideration. In another example, a human can review the digital image and provide feedback, such as information about abnormalities and requests for further imaging of certain aspects. Such information can be important, as it assists the caregiver taking the digital images to better understand the digital images and capture other relevant digital images while the patient is still available.

After the digital image is processed, the central server 106 sends the digital image back to the colposcope device 102 at operation 640.

Finally, at operation 650, the manipulated digital image is displayed by, for example, the image display module 218.

Figure 8:
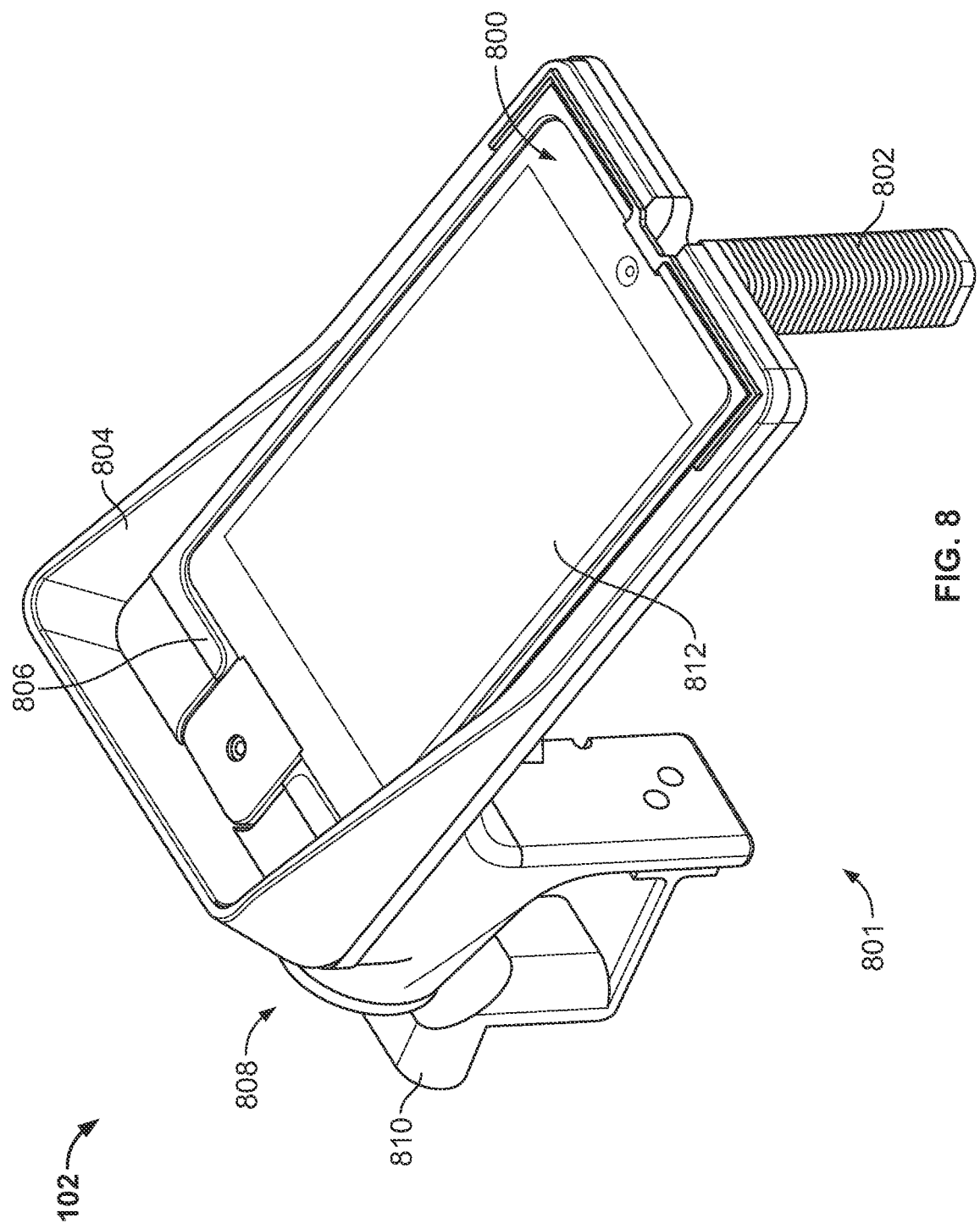
FIG. 8 shows an example of a colposcope device of FIG. 1.

Referring now to FIG. 8, the example colposcope device 102 is shown in more detail. In this example, the colposcope device 102 includes a housing 801 holding a portable computing device 800. In this example, the housing 801 includes a handle 802, a cradle 804, a cover 806, an optical capture device 808, and an illumination device 810. In this example, the portable computing device includes a display screen 812.

The handle 802 is configured to be gripped by a user of the colposcope device 102. In some embodiments, the handle 802 is also configured to be used to aim the colposcope device 102. In some embodiments, the handle 802 includes molded grips. In some embodiments, the handle is formed from plastic. In other embodiments, the handle is formed from a different rigid or semi-rigid material. However, some embodiments do not include a handle.

The cradle 804 is a physical structure and is configured to hold the portable computing device 800. In some embodiments, the cradle 804 includes a cavity that is sized to hold a specific type of portable computing device 800. For example, in some embodiments, the cradle 804 is configured to hold an iPad Mini from Apple Inc. of Cupertino, Calif. In other embodiments, the cradle 804 is configured to hold an iPhone or iPad, both also from Apple Inc. of Cupertino, Calif. Yet in other embodiments, the cradle 804 is configured to hold a different portable computing device 800, such as a tablet computer running an operating system like the Microsoft Windows operating system from Microsoft Corporation of Redmond, Wash., or the Android operating system from Google Inc. of Mountain View, Calif.

The cover 806 is a thin, flat surface and is configured to protect the display screen 812 of the portable computing device 800. In some embodiments, at least a portion of the cover 806 is transparent or translucent so that the display screen 812 of the portable computing device 800 can be seen. Yet in other embodiments, the cover 806 includes an opening through which the display screen 812 may be seen and touched. In some embodiments, the cover 806 is secured to the stand member using a hinge. In other embodiments, the cover 806 is disposed in the cradle 804 on a top surface of the portable computing device 800. In yet other embodiments, the cover 806 is configured to be secured to the cradle 804 with a screw or other fastener. However, some embodiments of the colposcope device 102 do not include a cover 806.

The optical capture device 808 is an optical device and is configured to direct light from external to the colposcope device 102 to a lens of the portable computing device 800, where the light can be captured by the image capture module 214. Additional details of the optical capture device 808 are shown in FIGS. 9-14.

The illumination device 810 is a device configured to provide light to an area in front of the colposcope device 102 so that the area may be imaged. In some embodiments, the illumination device 810 comprises one or more light emitting diodes. In other embodiments, the illumination device 810 comprises one or more incandescent bulbs. In other embodiments, the illumination device 810 comprises one or more fiber optic cables. Yet other embodiments of the illumination device 810 are possible as well. However, some embodiments of the colposcope device 102 do not include an illumination device 810.

In some embodiments, the display screen 812 is a touch-sensitive screen. However other embodiments of the portable computing device 800 are possible as well.

Figure 9:
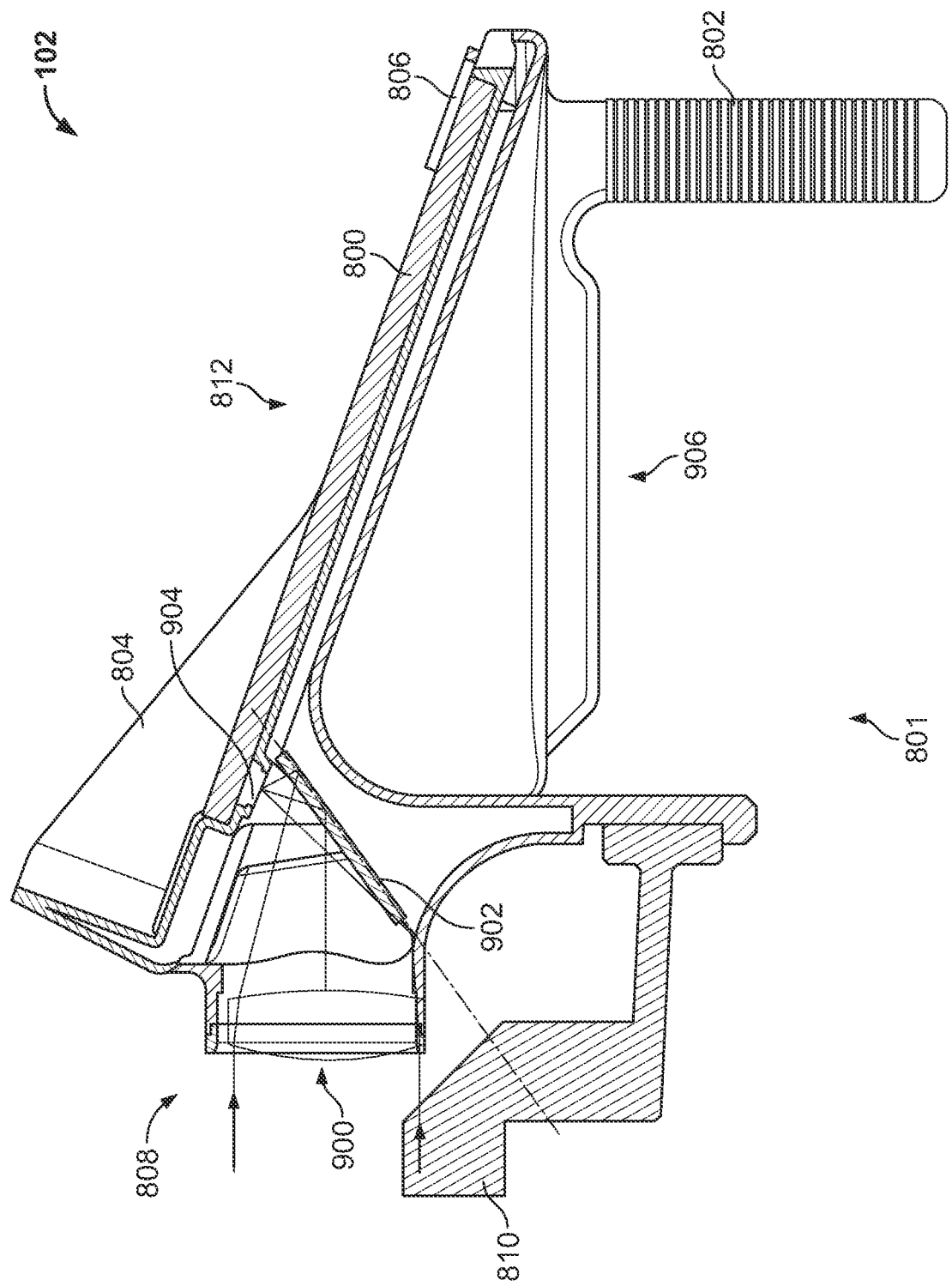
FIG. 9 shows a cross-sectional, side view of the example colposcope device of FIG. 8.

Referring now to FIG. 9, a cross-sectional, side view of the colposcope device 102 of FIG. 8 is shown. In particular, the optical capture device 808 is shown. The optical capture device 808 includes a lens 900 and reflection device 902. Also shown is the lens 904 of the portable computing device 800 and the attachment port 906 of the colposcope device 102.

Figure 10:
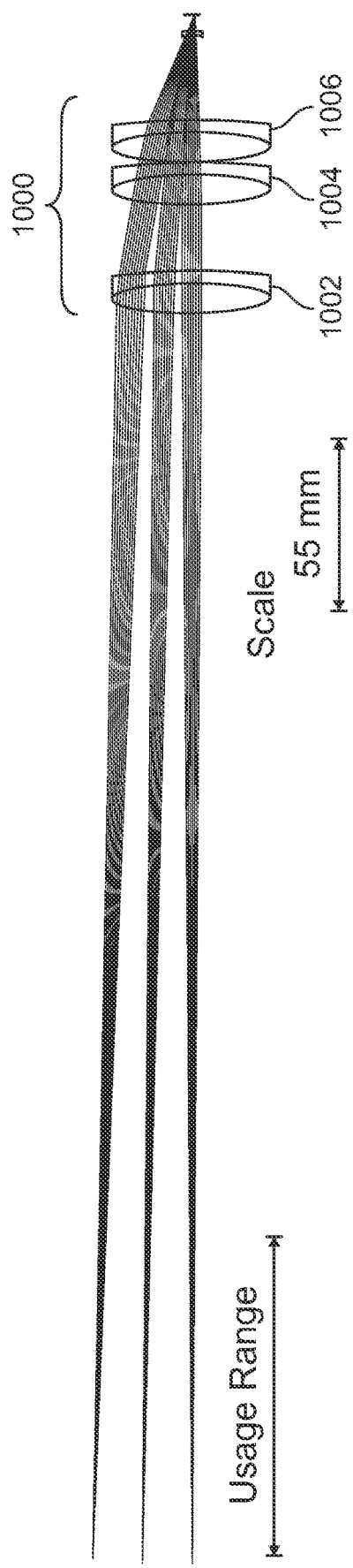
FIG. 10 shows an example of a constant magnification lens system of the optical capture device of the colposcope device of FIG. 1.
Figure 11:
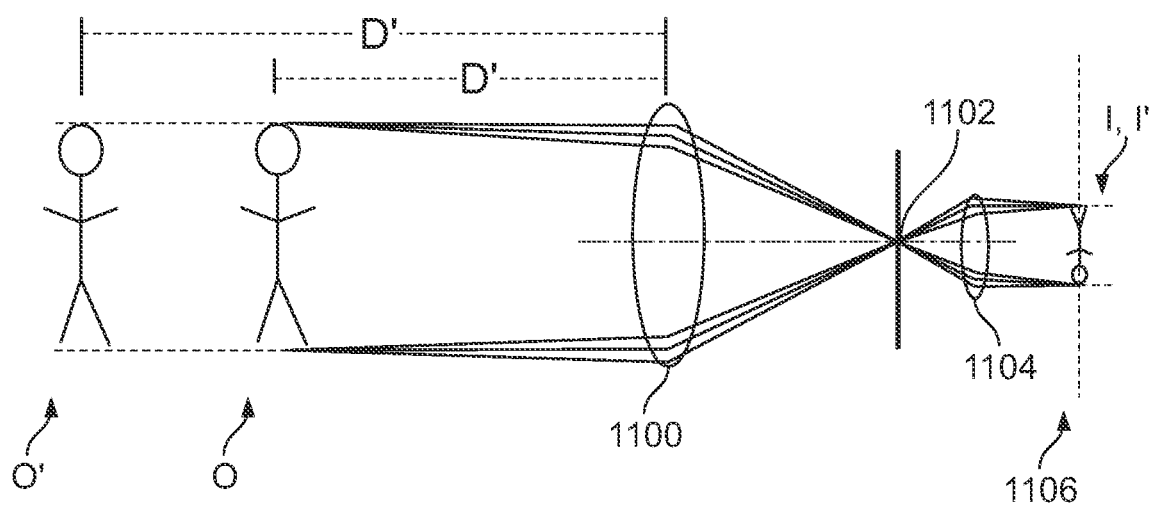
FIG. 11 shows another example of a constant magnification lens system of the optical capture device of the colposcope device of FIG. 1.

The lens 900 is an optical device that is configured to direct light from outside of the colposcope device 102 onto the reflection device 902. In some embodiments, the lens 900 is a constant magnification lens system. The size of the field of view in a constant magnification lens system does not change regardless of distance from the lens system. FIGS. 10 and 11 include additional details about these embodiments of lens 900.

The reflection device 902 is a device configured to reflect light into the lens 904 of the portable computing device 800. Examples of reflection device 902 include mirrors and prisms. Other embodiments of reflection device 902 are possible as well.

The attachment port 906 is a mechanical port and is configured to secure the colposcope device 102 to an external apparatus (e.g., a stand or swing arm). In some embodiments, the attachment port 906 is a female socket that is configured to mate with a male plug of the external apparatus. In some embodiments, the attachment port 906 is configured to rotatably couple to the external apparatus so that the colposcope device 102 rotates independently of the external apparatus. Other embodiments of the attachment port 906 are possible as well.

Referring now to FIG. 10, a constant magnification lens system 1000 is shown. The constant magnification lens system 1000 includes a first lens 1002, a second lens 1004, and a third lens 1006. The first lens 1002, the second lens 1004, and third lens 1006 are selected and disposed such that only light rays travelling in a direction substantially parallel to direction D1 are transmitted into lens 904 of the portable computing device 800 (either directly or indirectly, after being reflected by a reflection device 902). Because only light travelling in a direction substantially parallel to direction D1 is transmitted, the field of view of the constant magnification lens system 1000 does not change based on the distance between an object and the lens system 1000. In this manner, the size of a feature in an image captured by the image capture module 214 can be determined without regard to the distance between the lens system 1000 and the feature.

In some embodiments, the constant magnification lens system 1000 includes a collimating lens.

In an alternative design, the constant magnification lens system 1000 can include a tele-centric lens design having a front doublet and two lens singlets. A benefit of a tele-centric optical system is that it delivers constant magnification regardless where the object is within a given range of object-to-camera distances.

Referring now to FIG. 11, another example of a constant magnification lens system 1100 is shown. In this example, a constant magnification lens system 1100 directs light through an aperture 1102 and to a lens 1104, which directs the light onto an image plane 1106. In this example, the constant magnification lens system 1100 is detecting light reflected by a first object O that is a distance D away from the lens system 1100 and an identical second object O' that is a distance D' away from the lens system 1100. A first image I is created on the image plane 1106 of the first object O and a second image I' is created on the image plane 1106 of the second object O'. Despite the fact that the distance D is less than the distance D' and accordingly the first object O' is closer to the lens system 1100, the first image I and the second image I' are the same size on the image plane 1106.

Figure 12:
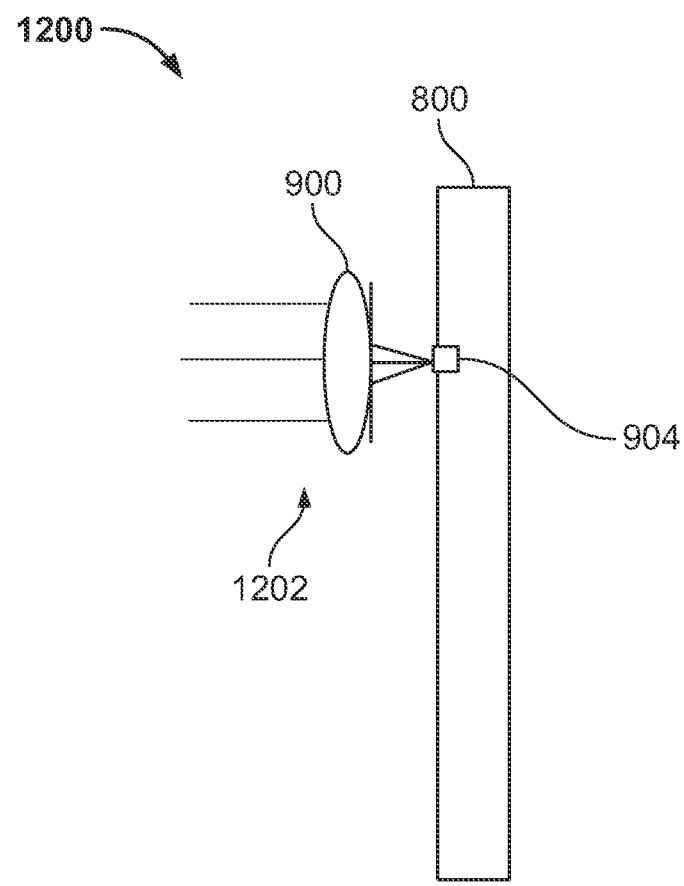
FIG. 12 shows an example of the optical capture device of the colposcope device of FIG. 1.

Referring now to FIG. 12, another embodiment of an optical capture device 1202 of a colposcope device 1200 is shown. This optical capture device 1202 is similar to the optical capture device 808 described above. This colposcope device 1200 is similar to the colposcope device 102 described above. However, to improve clarity, many other components of the colposcope device 1200 are not shown in this figure.

In the example shown, the lens 900 is aligned with the lens 904 of the portable computing device 800. The lens 900 is configured to focus light directly into the lens 904. With this embodiment of the colposcope device 1200, the lens 904 is aimed directly at the feature to be imaged. Because this embodiment of the optical capture device 1202 in colposcope device 1200 has few components, the colposcope device 1200 can be configured to rotate freely.

Figure 13:
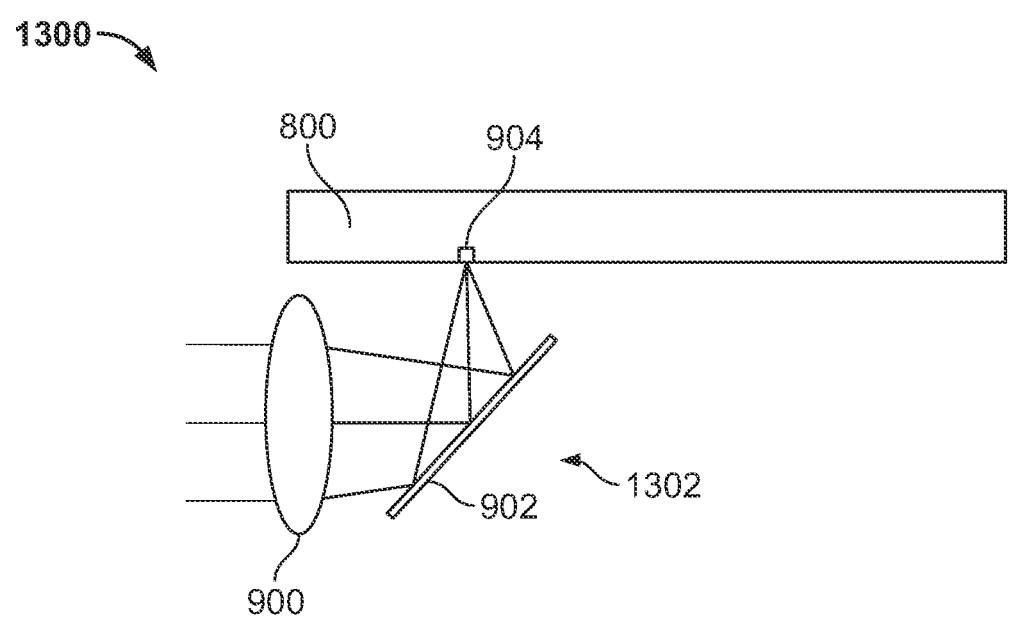
FIG. 13 shows another example of the optical capture device of the colposcope device of FIG. 1.

Referring now to FIG. 13, another embodiment of an optical capture device 1302 of a colposcope device 1300 is shown. This optical capture device 1302 is similar to the optical capture device 808 described above. This colposcope device 1300 is similar to the colposcope device 102 described above. However, to improve clarity, many other components of the colposcope device 1300 are not shown in this figure.

In the example shown, the optical capture device 1302 includes the lens 900 and the reflection device 902. The orientation of the lens 900 is perpendicular to the lens 904 of the portable computing device 800. The reflection device 902 is configured to reflect the light transmitted by the lens 900 onto the lens 904. In some embodiments, the reflection device 902 is a mirror oriented at a forty-five degree angle. However other embodiments of the reflection device 902 are possible as well.

This arrangement may be advantageous in situations where the lens 904 of the portable computing device 800 is opposite the display screen 812. Because the lens 904 of the portable computing device 800 does not need to be aimed directly at the feature being imaged, the user of the colposcope device may view and interact with the portable computing device 800 at a more comfortable angle.

Figure 14:
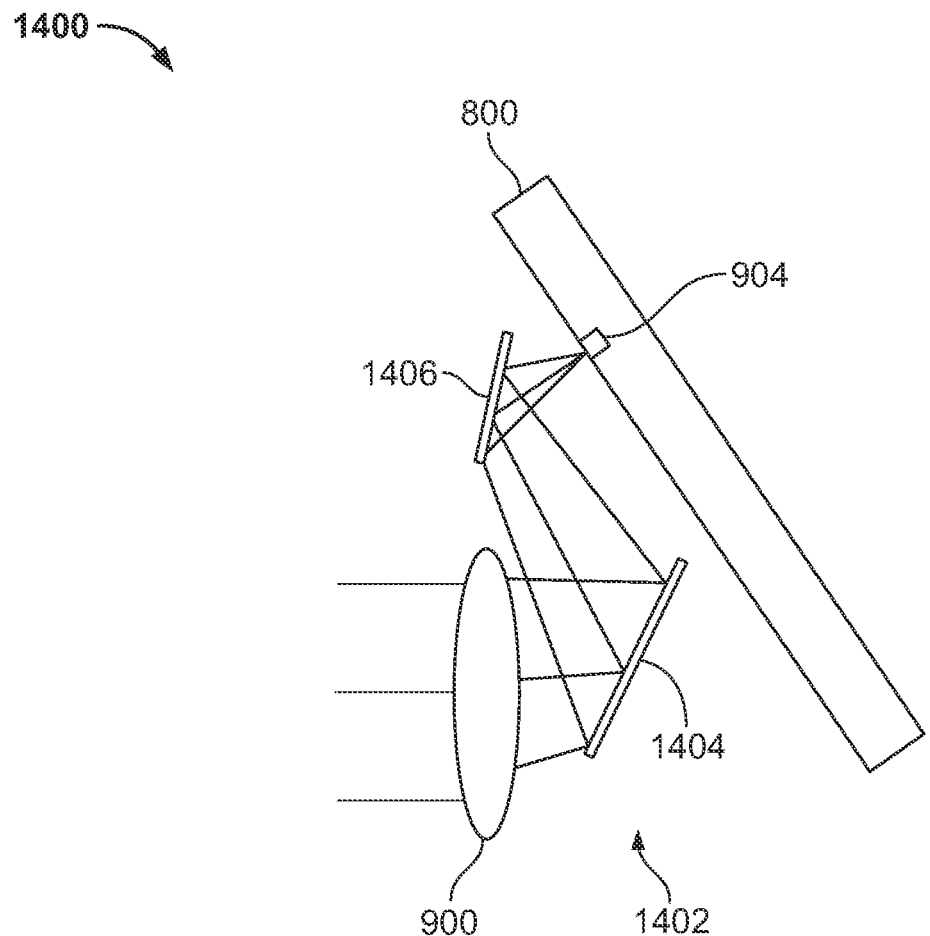
FIG. 14 shows another example of the optical capture device of the colposcope device of FIG. 1.

Referring now to FIG. 14, another embodiment of an optical capture device 1402 of a colposcope device 1400 is shown. This optical capture device 1402 is similar to the optical capture device 808 described above. This colposcope device 1400 is similar to the colposcope device 102 described above. However, to improve clarity, many other components of the colposcope device 1400 are not shown in this figure.

In the example shown, the optical capture device 808 includes the lens 900, a first reflection device 1404, and a second reflection device 1406. The orientation of lens 900 is rotated by approximately forty-five degrees from the lens 904 of the portable computing device 800. However, other embodiments with the lens 900 rotated by other angles are possible as well. The light directed by lens 900 is reflected by the first reflection device 1404 to the second reflection device 1406, which then reflects the light into the lens 904. Although there are two reflecting devices in the example shown, other embodiments with more reflecting devices are possible as well.

Figure 15:
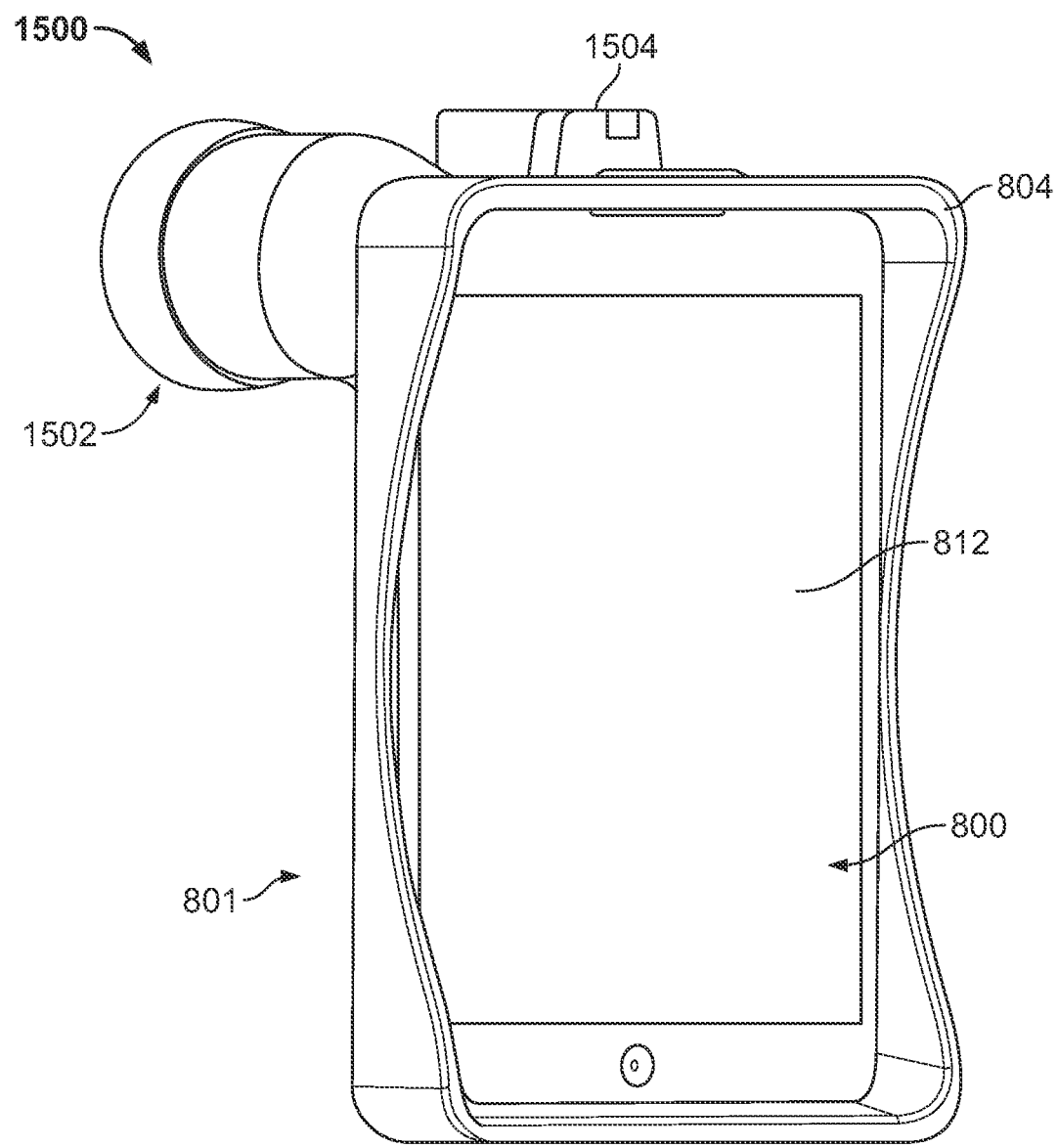
FIG. 15 shows a front, isometric projection of another example of the colposcope device of FIG. 1.

Referring now to FIG. 15, a front, isometric projection of another embodiment of a colposcope device 1500 is shown. In this example, the colposcope device 1500 includes an optical capture device 1502 and an attachment port 1504. The optical capture device 1502 is similar to the optical capture device 808 described above. The attachment port 1504 is a mechanical port and is configured to secure the colposcope device 1500 to an external apparatus (e.g., a stand or swing arm). In some embodiments, the attachment port 1504 is a female socket that is configured to mate with a male plug of the external apparatus. Other embodiments of the attachment port 1504 are possible as well.

Figure 16:
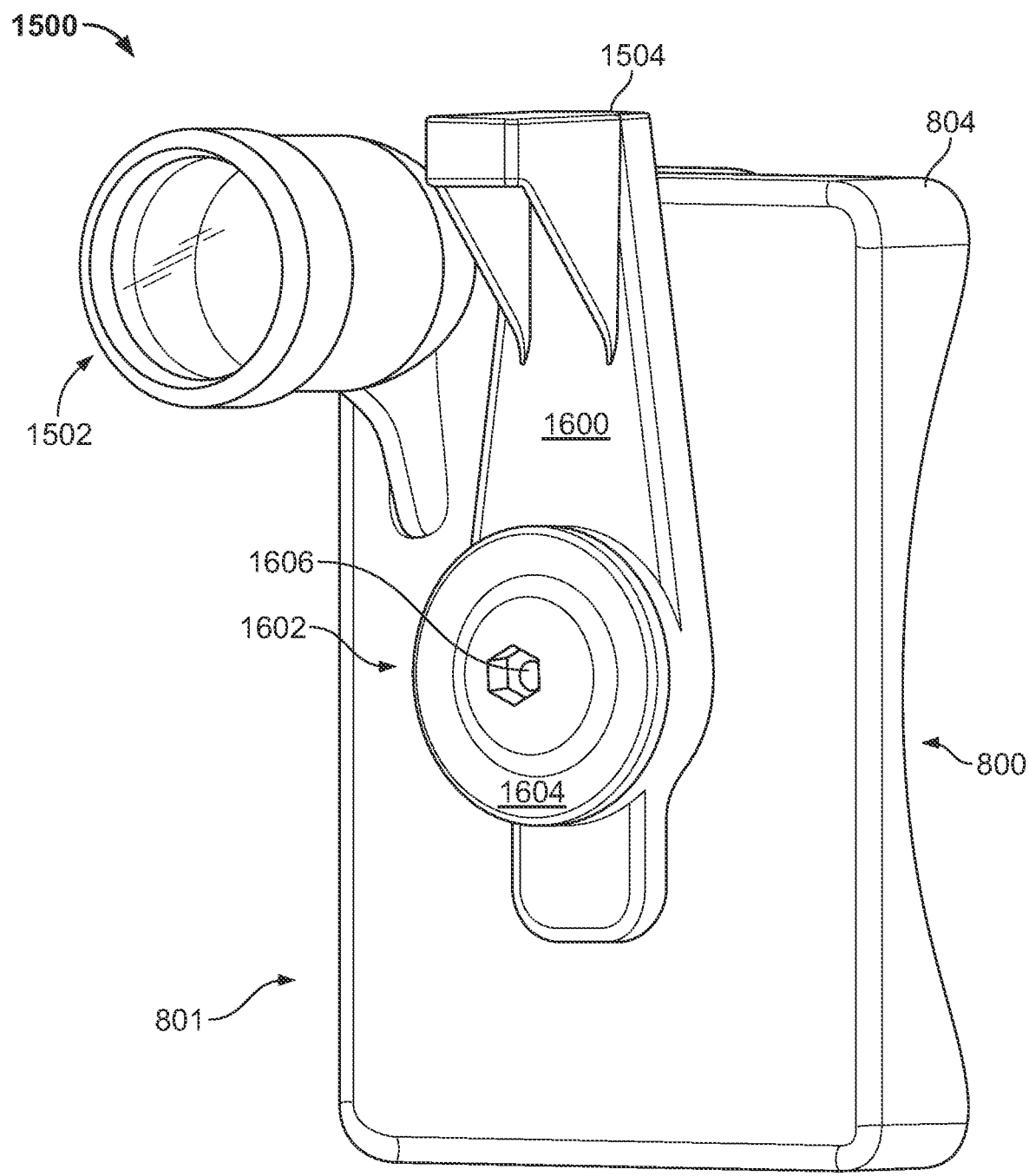
FIG. 16 shows a rear, isometric projection of the example colposcope device of FIG. 15.

Referring now to FIG. 16, a rear, isometric projection of the embodiment of the colposcope device 1500 of FIG. 15 is shown.

In this embodiment, the attachment port 1504 is coupled to an arm 1600. The arm 1600 is coupled to the cradle 804 at a joint 1602. The joint 1602 includes a plate 1604. The plate 1604 includes an aperture 1606. The aperture 1606 is configured to be aligned with an aperture (not shown) in the arm 1600, both of which are configured to, in combination with a fastener (not shown), secure the arm 1600 to the cradle 804. In some embodiments, the joint 1602 is a rotational joint and is configured to rotatably couple the arm 1600 to the cradle 804. In this manner, the orientation of the portable computing device 800 can be changed while the colposcope device 1500 is coupled to an external apparatus. Further, in some embodiments, either the arm 1600 or the cradle 804 includes four detents (not shown) disposed at ninety degree intervals about the aperture 1606. The detents are configured to arrest the rotational movement of the cradle 804 at predetermined orientations. In other embodiments, the attachment port 1504 is coupled to the cradle 804 using other mechanisms.

Figure 17:
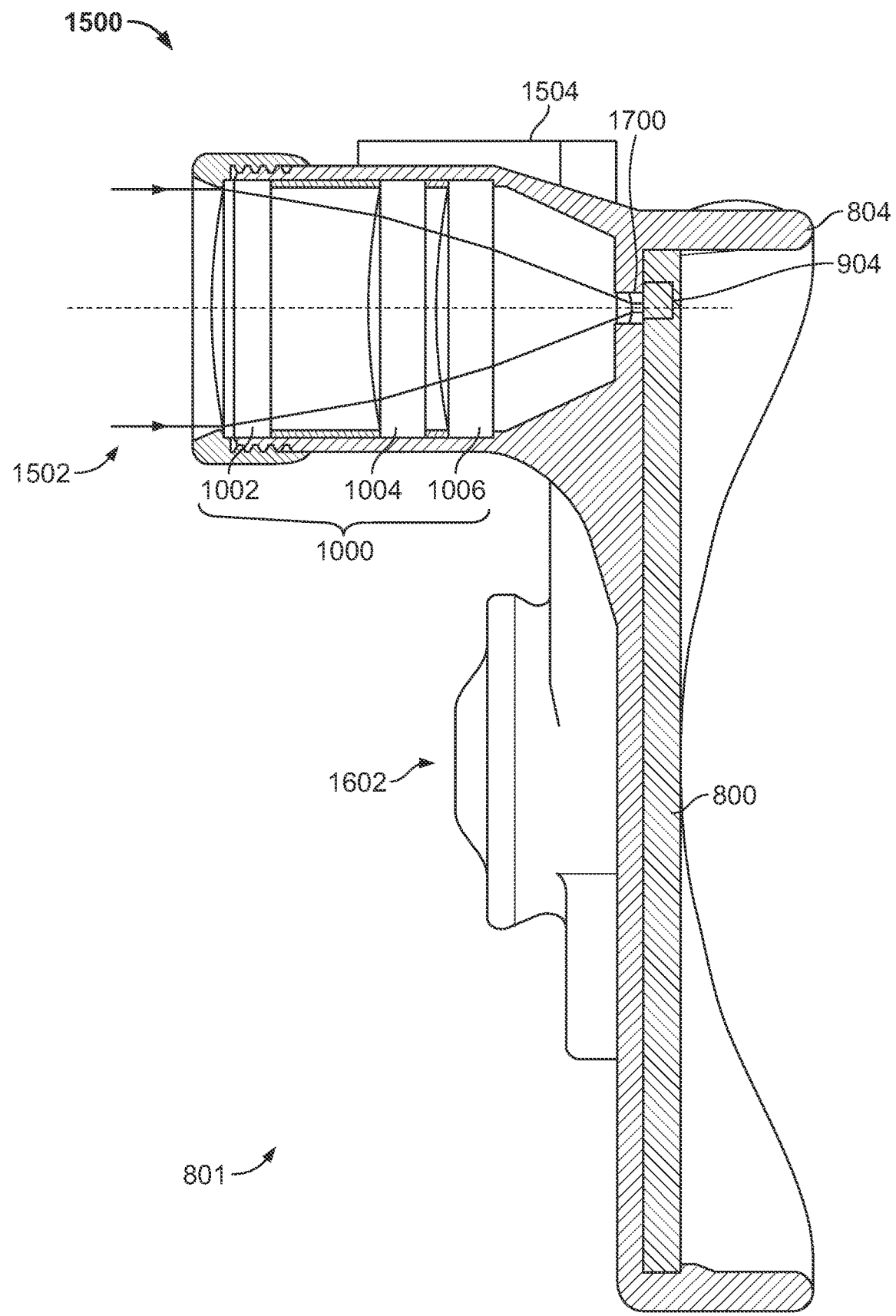
FIG. 17 shows a side, cross-sectional view of the example colposcope device of FIG. 15.

Referring now to FIG. 17, a side, cross-sectional view of the embodiment of the colposcope device 1500 of FIG. 15 is shown. In particular, the optical capture device 1502 is shown. In this embodiment, the optical capture device 1502 includes the constant magnification lens system 1000, including the first lens 1002, the second lens 1004, and the third lens 1006. Also shown is an aperture 1700 of the housing 801.

The constant magnification lens system 1000 is shown and described in greater detail with respect to FIGS. 10 and 11. In the embodiment shown, the optical capture device 1502 is configured to focus light from external to the colposcope device 1500 through the aperture 1700 and onto the lens 904 of the portable computing device 800.

Figure 18:
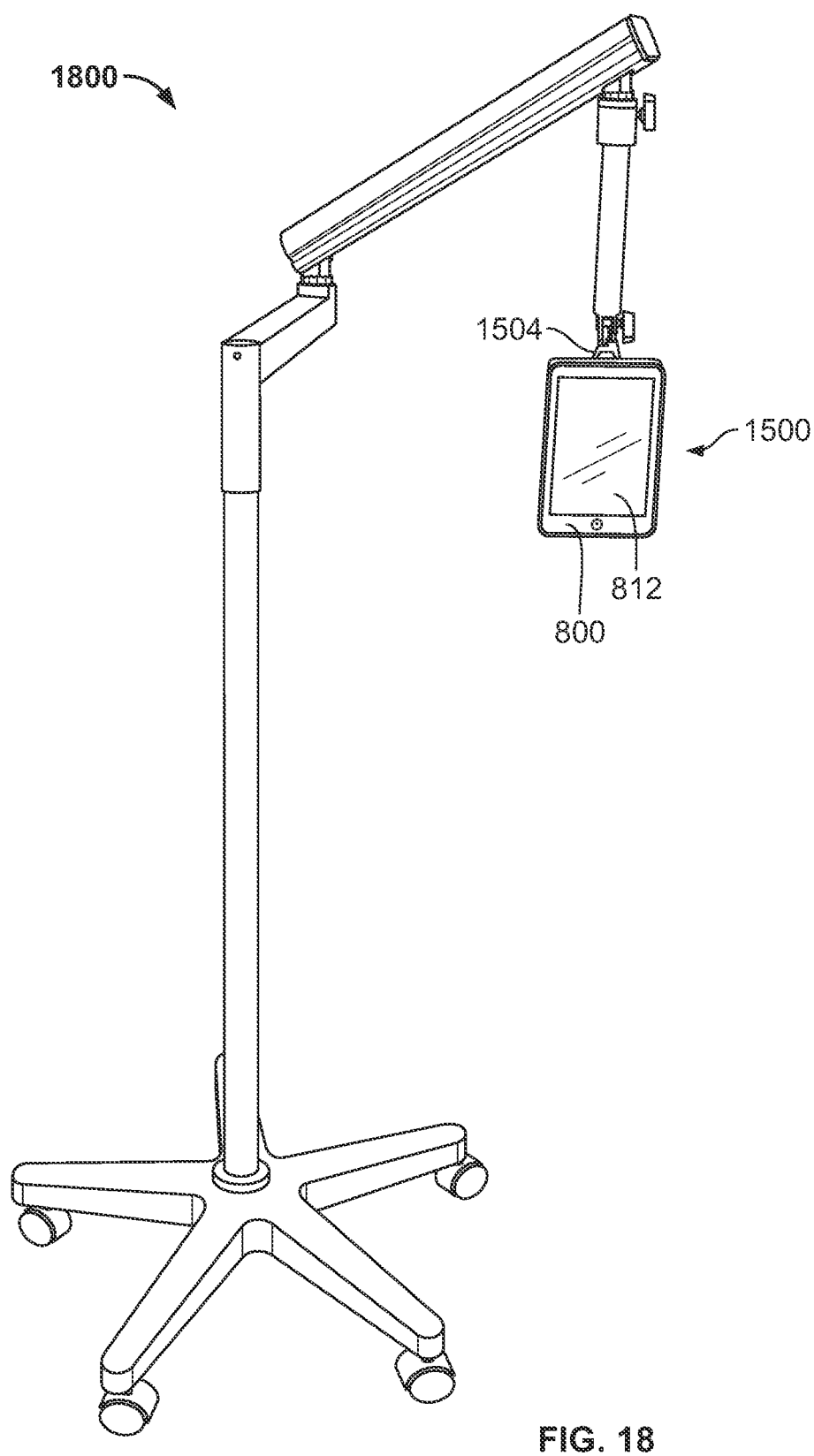
FIG. 18 shows an example of the colposcope device of FIG. 15 coupled to a swing-arm stand.

Referring now to FIG. 18, a view of the embodiment of the colposcope device 1500 shown in FIG. 15 is shown coupled to one embodiment of the stand module 212. This stand module 212 includes an external swing-arm stand 1800. The colposcope device 102 is coupled to the swing-arm stand 1800 at the attachment port 1504. As shown in FIG. 18, the colposcope device 1500 is oriented vertically, allowing the display screen 812 of the portable computing device 800 to operate in a portrait mode.

Figure 19:
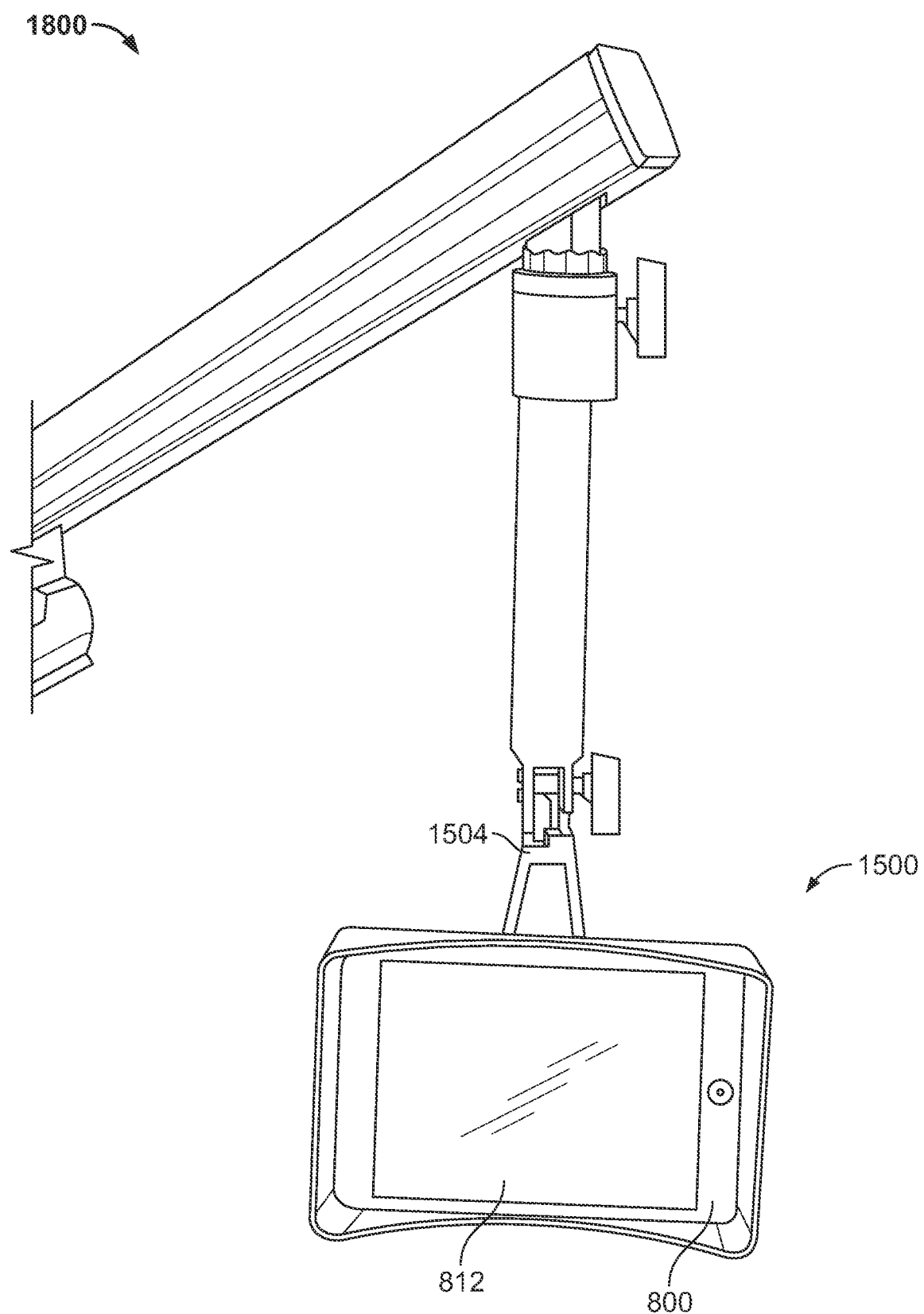
FIG. 19 shows another example of the colposcope device of FIG. 15 coupled to a swing-arm stand.

Referring now to FIG. 19, another view of the embodiment of the colposcope device 1500 shown in FIG. 15 is shown coupled to the external swing-arm stand 1800. The colposcope device 1500 is again coupled to the swing-arm stand 1800 at the attachment port 1504. However in FIG. 19, the colposcope device 1500 is oriented horizontally, allowing the display screen 812 of the portable computing device 800 to operate in a landscape mode.

Figure 20:
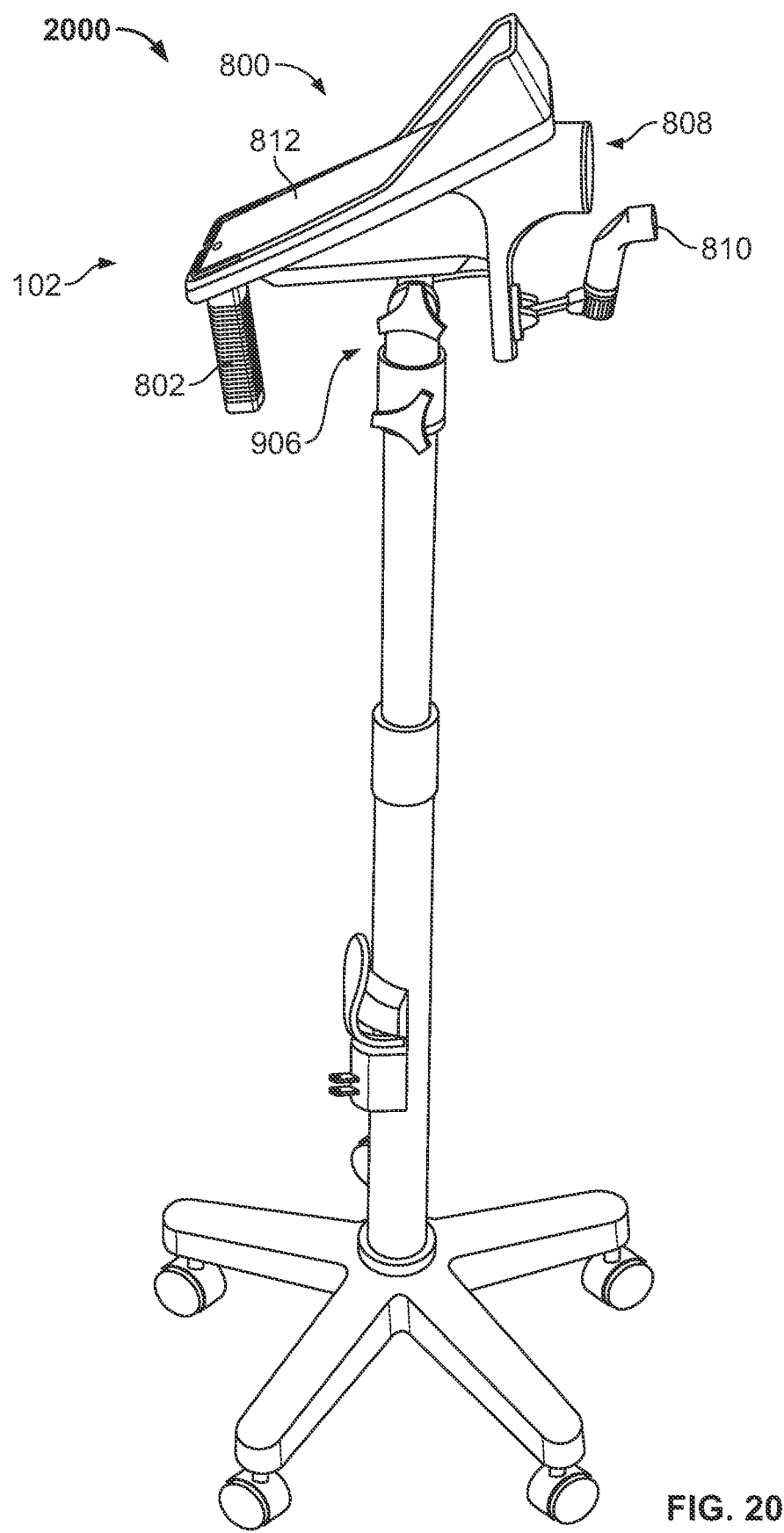
FIG. 20 shows an example of the colposcope device shown in FIG. 8 coupled to a vertical stand.

Referring now to FIG. 20, a view of the embodiment of the colposcope device 102 shown in FIG. 8 is shown coupled to one embodiment of the stand module 212. This stand module 212 includes an external vertical stand 2000.

The colposcope device 102 is coupled to the vertical stand 2000 at the attachment port 906. In some embodiments, the colposcope device 102 is rotatably coupled to the vertical stand 2000 at the attachment port 906 and configured to a permit a user to use the handle 802 to aim the optical capture device 808 and illumination device 810. In the embodiment shown, the display screen 812 of the portable computing device 800 faces substantially upward and is configured to be viewed from above.

Figure 21:
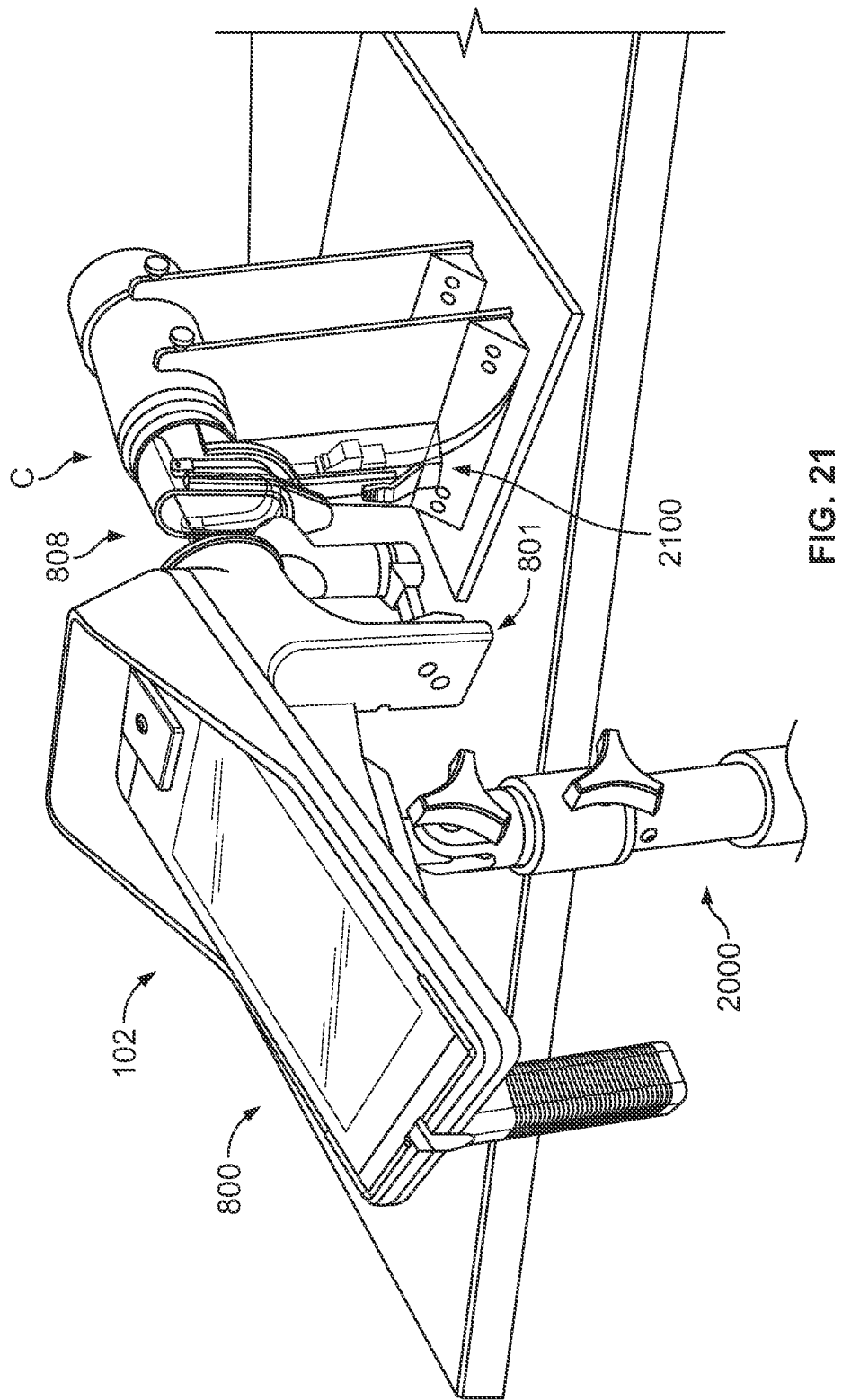
FIG. 21 shows an example of the colposcope of FIG. 8 being used with a speculum to a view a cavity.

Referring now to FIG. 21, the embodiment of the colposcope device 102 shown in FIG. 8 is shown being used to a view a cavity C, representative of a body cavity, such as a vagina. Also shown is a speculum 2100.

As shown in FIG. 21, the colposcope device 102 is coupled to the vertical stand 2000 and disposed so that the optical capture device 808 is configured to view the cavity C through the speculum 2100. The speculum 2100 is a mechanical device and is configured to be inserted into the cavity C. The speculum 2100 is shown and described in more detail with reference to FIG. 23.

Figure 22:
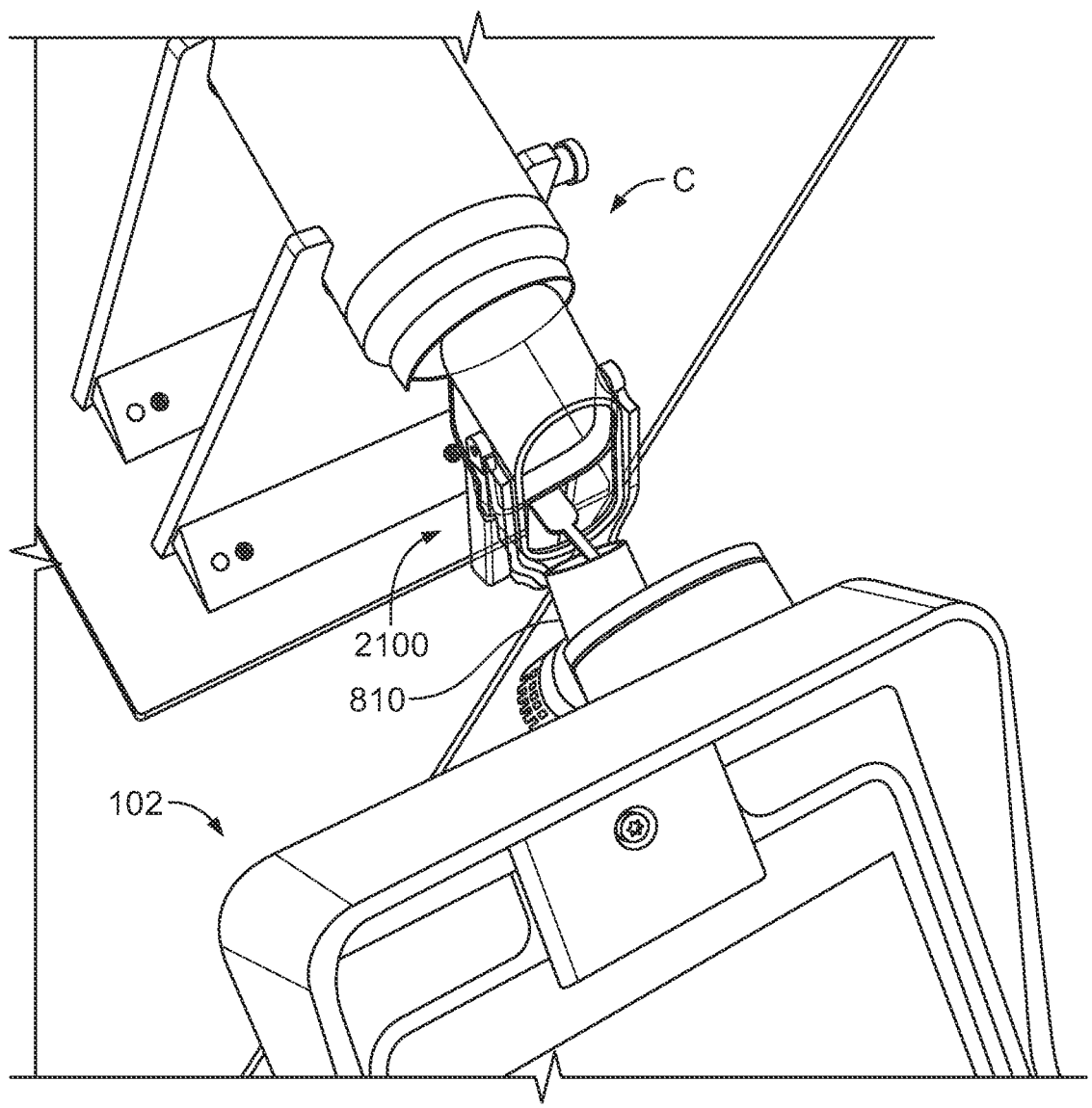
FIG. 22 shows a top view of the example of the colposcope device of FIG. 8 being used with a speculum to a view a cavity.

Referring now to FIG. 22, a top view of the embodiment of the colposcope device 102 shown in FIG. 8 being used to a view a cavity C is shown. Also shown is the speculum 2100.

As shown in FIG. 22, the optical capture device 808 of the colposcope device 102 is aimed through the speculum 2100 to view the cavity C. Additionally, the illumination device 810 is aimed to transmit light through the speculum 2100 and into the cavity C. However, in some embodiments, colposcope device 102 does not include the illumination device 810. In some embodiments, the speculum 2100 includes an illumination device instead of or in addition to the illumination device 810 of the colposcope device 102.

Figure 23:
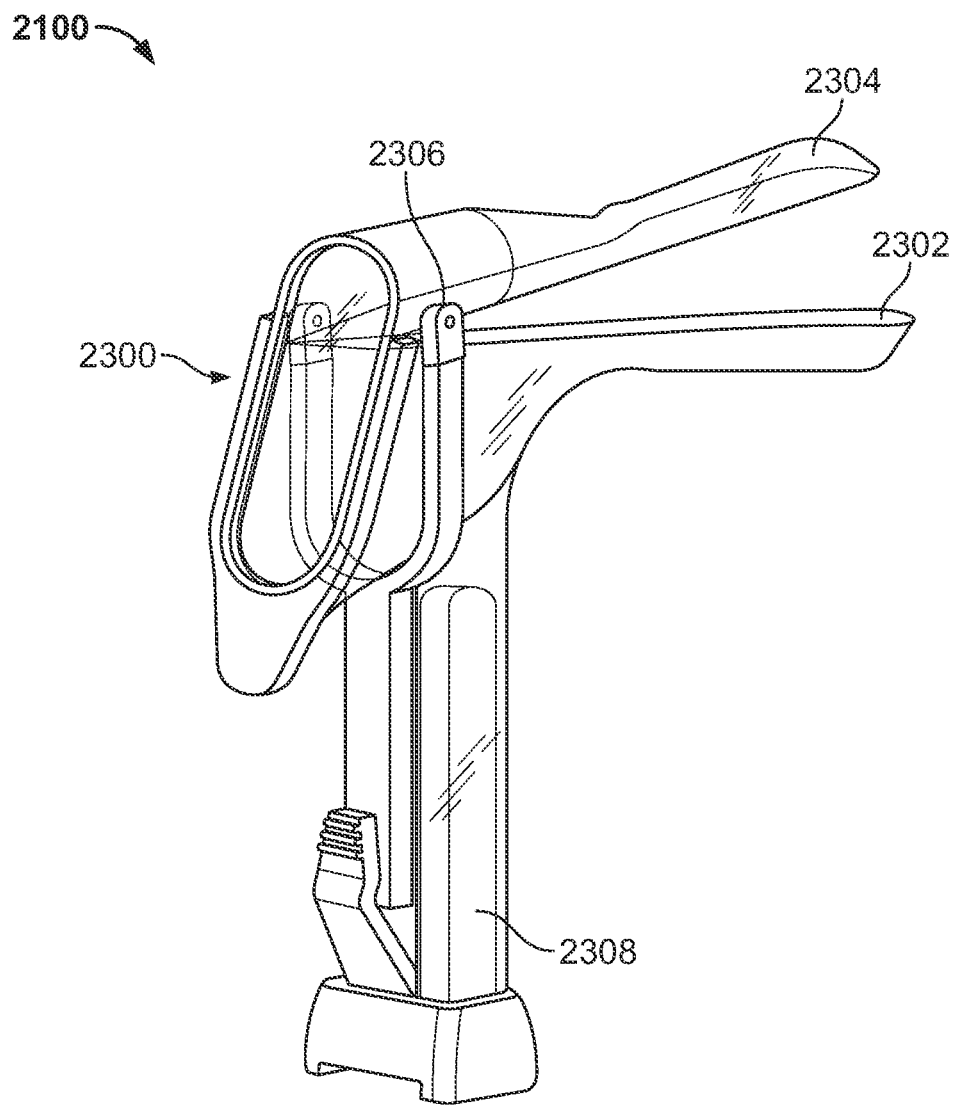
FIG. 23 shows an example of the speculum of FIG. 21.

Referring now to FIG. 23, an embodiment of the speculum 2100 is shown. As discussed above, the speculum 2100 is a mechanical device and is configured to be inserted into a body cavity. In some embodiments, the speculum 2100 includes a port 2300, a first blade 2302, a second blade 2304, a hinge 2306, and an illumination device 2308. The first blade 2302 and the second blade 2304 are coupled at a hinge 2306 and are configured to move between a closed position and an open position. While in the closed position, the speculum 2100 may more easily be inserted into a body cavity. After the speculum 2100 is inserted, the first blade 2302 and the second blade 2304 may be moved to the open position to facilitate viewing and investigation of the body cavity.

The illumination device 2308 is a device and is configured to produce light and direct that light through the speculum 2100 to illuminate the body cavity. In some embodiments, the illumination device 2308 comprises one or more light emitting diodes. In other embodiments, the illumination device 2308 comprises one or more incandescent bulbs. In other embodiments, the illumination device 2308 comprises one or more fiber optic cables. Yet other embodiments of the illumination device 2308 are possible as well.

In some embodiments, using the colposcope device 102 with a speculum 2100 that includes an illumination device 2308 has the benefit that light provided by the illumination device 2308 is not occluded by the speculum 2100 like light provided by a source behind the speculum 2100 might be. Additionally, in some embodiments, when used with a speculum 2100 that includes an illumination device 2308, the colposcope device 102 is wireless and does not require an external battery source because some embodiments of the portable computing device 800 include an internal battery.

However, some embodiments of the speculum 2100 do not include an illumination device 2308. For example, in some embodiments, the colposcope device 102 is configured to be used with a traditional metal speculum.

In some embodiments, the speculum 2100 is a KleenSpec Disposable Vaginal Speculum from Welch Allyn of Skaneateles Falls, N.Y., and includes the KleenSpec Cordless Illumination System also from Welch Allyn of Skaneateles Falls, N.Y., although other systems can be used.

In some embodiments, the colposcope devices described herein can be used to capture additional information during examination. For example, in one embodiment, the colposcope devices are configured to capture video and/or audio during examination. In such an instance, video of the examination is captured, along with audio from the caregiver and/or patient. The video and/or audio can be used, for example, for consultation recording and/or for teaching purposes.

Although various embodiments are described herein, those of ordinary skill in the art will understand that many modifications may be made thereto within the scope of the present disclosure. Accordingly, it is not intended that the scope of the disclosure in any way be limited by the examples provided.

What is claimed is:

1. A housing for a colposcope device, comprising:
   a cradle, the cradle being configured to hold a portable computing device having a display screen and a lens, the cradle including an aperture providing access to the lens of the portable computing device;
   an optical capture device attached to the cradle, the optical capture device including a constant magnification lens system, the constant magnification lens system being configured to direct light from outside of the colposcope device, through the aperture of the cradle, and to the lens of the portable computing device; and
   an attachment port attached to the cradle, the attachment port being a mechanical port configured to be removably and rotatably coupled to an external stand to allow the display screen to operate in a portrait mode and in a landscape mode while the colposcope device is coupled to the external stand.

2. The housing of claim 1, further comprising an illumination device, the illumination device being configured to produce the light.

3. The housing of claim 1, wherein the constant magnification lens system comprises at least three optical lenses.

4. The housing of claim 3, wherein the constant magnification lens system further comprises a reflecting device.

5. The housing of claim 4, wherein the reflecting device is a mirror.

6. The housing of claim 4, wherein the reflecting device is a prism.

7. A colposcope device, comprising:
   a portable computing device, the portable computing device including a camera, a display screen, and a processor; and
   a housing, the housing including:
      a cradle configured to hold the portable computing device, the cradle including an aperture, the aperture being configured to permit light from outside of the colposcope device to reach the camera of the portable computing device;
      an attachment port attached to the cradle, the attachment port being a mechanical port configured to be removably and rotatably coupled to an external stand to allow the display screen of the portable computing device to operate in a portrait mode and in a landscape mode while the colposcope device is coupled to the external stand; and an optical capture device including a constant magnification lens system, the constant magnification lens system being configured to direct the light from outside of the colposcope device and through the aperture of the cradle.

8. The device of claim 7, further comprising an illumination device, the illumination device being configured to produce the light.

9. The device of claim 7, wherein the constant magnification lens system comprises at least three optical lenses.

10. The device of claim 9, wherein the constant magnification lens system further comprises a reflecting device.

11. The device of claim 10, wherein the reflecting device is a mirror.

12. The device of claim 10, wherein the reflecting device is a prism.

13. A colposcope system, comprising:
a speculum, the speculum including a port and an illumination device;
a portable computing device, the portable computing device including a camera, a display screen, and a processor; and
a housing, the housing comprising:
a cradle, the cradle being configured to hold the portable computing device, the cradle including an aperture, the aperture being configured to permit light from the port of the speculum to reach the camera of the portable computing device;

an attachment port attached to the cradle, the attachment port being a mechanical port configured to be removably and rotatably coupled to an external stand to allow the display screen of the portable computing device to operate in a portrait mode and in a landscape mode while the colposcope device is coupled to the external stand; and an optical capture device attached to the cradle, the optical capture device including a constant magnification lens system, the constant magnification lens system being configured to direct the light from the port of the speculum, through the aperture of the cradle, and to the camera of the portable computing device;

wherein the optical capture device is configured to capture the light through the port of the speculum.

14. A system of claim 13, further comprising:

an image processing module programmed to digitally process the digital image, including:

a filter module programmed to filter certain aspects of the digital image; and an overlay module programmed to allow the digital image to be annotated.

15. The system of claim 14, wherein the portable computing device is further configured to capture video and audio during examination of a patient.

16. The system of claim 13, wherein the constant magnification lens system further comprises a reflecting device.

* * * * *